(12) United States Patent
Yamaya et al.

(10) Patent No.: US 12,251,252 B2
(45) Date of Patent: Mar. 18, 2025

(54) RADIATION DETECTOR

(71) Applicant: National Institutes for Quantum Science and Technology, Chiba (JP)

(72) Inventors: Taiga Yamaya, Chiba (JP); Miwako Takahashi, Chiba (JP)

(73) Assignee: National Institutes for Quantum Science and Technology, Chiba (JP)

( * ) Notice: Subject to any disclaimer, the term of this patent is extended or adjusted under 35 U.S.C. 154(b) by 221 days.

(21) Appl. No.: 18/002,510

(22) PCT Filed: Jun. 3, 2021

(86) PCT No.: PCT/JP2021/021132
§ 371 (c)(1),
(2) Date: Dec. 20, 2022

(87) PCT Pub. No.: WO2021/261198
PCT Pub. Date: Dec. 30, 2021

(65) Prior Publication Data
US 2023/0301612 A1 Sep. 28, 2023

(30) Foreign Application Priority Data
Jun. 25, 2020 (JP) .................................. 2020-109529

(51) Int. Cl.
*A61B 6/42* (2024.01)
*A61B 6/40* (2024.01)
(Continued)

(52) U.S. Cl.
CPC ............ *A61B 6/425* (2013.01); *A61B 6/4057* (2013.01); *A61B 6/4258* (2013.01); *A61B 6/50* (2013.01);
(Continued)

(58) Field of Classification Search
CPC ..... A61B 6/425; A61B 6/4057; A61B 6/4258; A61B 6/50; A61B 17/29; A61B 90/39;
(Continued)

(56) References Cited

U.S. PATENT DOCUMENTS 5,014,708 A 5/1991 Hayashi et al.
5,331,961 A 7/1994 Inaba
(Continued)

FOREIGN PATENT DOCUMENTS

CN 202437122 U * 9/2012
CN 203408050 U * 1/2014
(Continued)

OTHER PUBLICATIONS

EPO, Extended European Search Report for corresponding European Patent Application No. 21828239.0 dated Jun. 18, 2024, 11 pages.
(Continued)

*Primary Examiner* — Edwin C Gunberg
*Assistant Examiner* — Richard O Toohey
(74) *Attorney, Agent, or Firm* — NK Patent Law

(57) ABSTRACT

Provided is a radiation detector that can allow an operator to more accurately identify a position of a body tissue into which radionuclides have been taken. A radiation detector includes: a probe which has a radiation detection element housed therein and which is insertable into a body; a reporting part provided to the probe; and a control part configured to cause the reporting part to operate in accordance with a result of detection of radiation, the detection being made by the radiation detection element.

17 Claims, 13 Drawing Sheets

(51) Int. Cl.
*A61B 6/50* (2024.01)
*A61B 17/29* (2006.01)
*G01T 1/161* (2006.01)
*G01T 1/20* (2006.01)

(52) U.S. Cl.
CPC .............. *A61B 17/29* (2013.01); *G01T 1/161* (2013.01); *G01T 1/2002* (2013.01)

(58) Field of Classification Search
CPC ............ A61B 90/06; A61B 2017/2825; A61B 2017/2926; A61B 2090/0807; A61B 2090/392; G01T 1/161; G01T 1/2002; G01T 1/2985
See application file for complete search history.

(56) References Cited

U.S. PATENT DOCUMENTS

| | | | |
|---|---|---|---|
| 2002/0117627 A1 | | 8/2002 | Jimbo et al. |
| 2011/0208049 A1 | | 8/2011 | Turner |
| 2016/0170035 A1* | | 6/2016 | Yarnall ............... A61B 6/12 600/436 |
| 2020/0046305 A1* | | 2/2020 | Speeg ................ G01T 1/244 |
| 2020/0268329 A1* | | 8/2020 | Sorger ............... A61B 6/4417 |
| 2020/0268389 A1* | | 8/2020 | Sgroi, Jr. ........... A61B 17/1155 |
| 2022/0008118 A1* | | 1/2022 | Lyons ............... A61B 18/1442 |
| 2022/0039683 A1* | | 2/2022 | Harmer ............. A61B 5/742 |

FOREIGN PATENT DOCUMENTS

| | | | |
|---|---|---|---|
| JP | 2080063 A | | 3/1990 |
| JP | 2259589 A | | 10/1990 |
| JP | 10325876 A | | 12/1998 |
| JP | 3041086 B2 | | 5/2000 |
| JP | 2001228256 A | | 8/2001 |
| JP | 2002257938 A | | 9/2002 |
| JP | 2003079634 A | | 3/2003 |
| JP | 2005043156 A | * | 2/2005 |
| WO | 2018184034 A1 | | 10/2018 |

OTHER PUBLICATIONS

ISA/JP, International Search Report for corresponding PCT Patent Application No. PCT/JP2021/021132, mailed Jul. 20, 2021, 6 pages.

ISA/JP, Written Opinion for corresponding PCT Patent Application No. PCT/JP2021/021132, mailed Jul. 20, 2021, 8 pages.

Miwako Takahashi et al.: "Development of the performance of radiographs to enable diagnosis of intraoperative lymph node metastases", Oct. 30, 2020, 2 pages.

Miwako Takahashi et al. "Forceps type mini-PET system for intra-operative lymph node diagnosis: conceptual design", NIRS-QST, Furukawa Scintitech Co., University of Tokyo, 2020, 2 pages.

Shuntaro Yoshimura et al.: "One-by-One Comparison of Lymph Nodes Between 18F-FDG Uptake and Pathological Diagnosis in Esophageal Cancer", Clinical Nuclear Medicine, vol. 00, No. 00, Month 2020, https://www.ncbi.nlm.nih.gov/pmc/articles/PMC7469872/, 6 pages.

Miwako Takahashi, Principal Researcher: "Nuclear medicine for intraoperative lymph node diagnosis", Jan. 23, 2021, pp. 83-90.

Douglas A. Murrey, Jr et al.: "Perioperative 18F-fluorodeoxyglucose-guided imaging using the becquerel as a quantitative measure for optimizing surgical resection in patients with advanced malignancy," The American Journal of Surgery, 198, pp. 834-840, 2009.

Kunihiko Yokoyama et al.: "Detection of isotopes in sentinel lymph nodes", Nikko Medical Daily vol. 46, No. 2, No. 212-217, 2001, 13 pages.

* cited by examiner

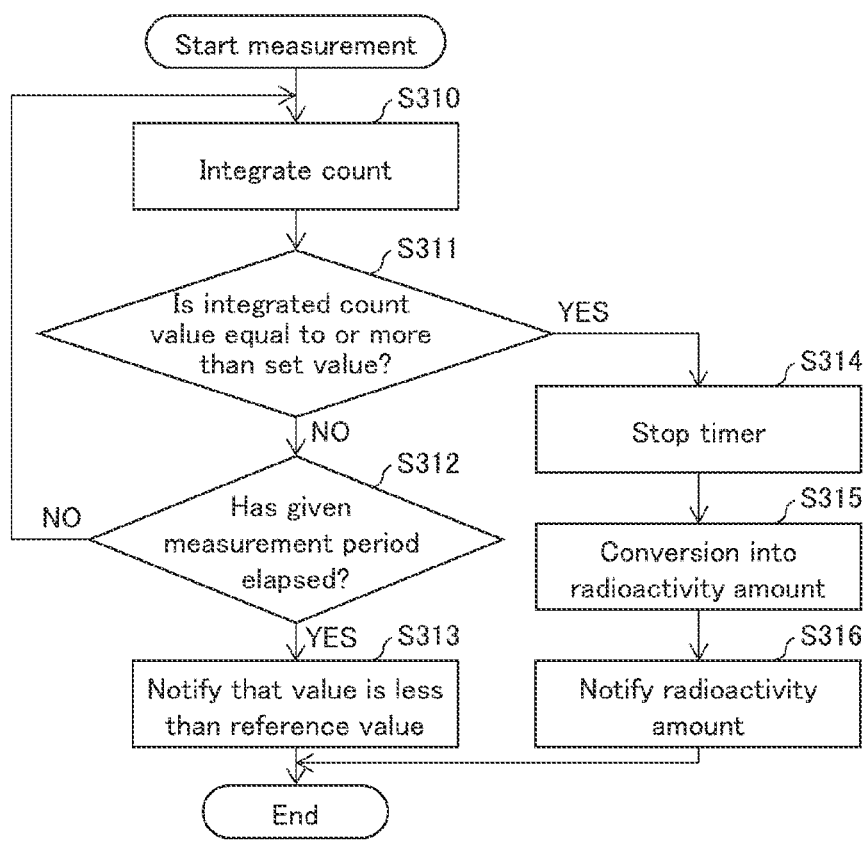

RADIATION DETECTOR

CROSS-REFERENCE TO RELATED APPLICATIONS

This application is a U.S. National Stage Application of International Patent Application No. PCT/JP2021/021132, filed on Jun. 3, 2021, which claims priority to Japanese Patent Application No. 2020-109529, filed on Jun. 25, 2020, the entire contents of all of which are incorporated by reference herein.

TECHNICAL FIELD

The present invention relates to a radiation detector.

BACKGROUND ART

Heretofore, cancer cells in which a certain compound is likely to be taken or tissues in which compounds of a certain size are likely to be accumulated have been known. In order to identify the position of such a cancer cell or such a tissue, an attempt to administer, to a patient, a compound including radionuclides and identify the position thereof by a gamma camera has been made. For example, there has been known a method for administering, to a patient, compound formulations containing $^{99m}$Tc, identifying a lymph node in which the compounds are accumulated, and resecting the lymph node. In order to carry out this method, Non-Patent Literature 1 discloses a portable gamma camera with which determination of whether or not a cancer has spread to a sentinel lymph node can be made during a surgery.

Meanwhile, Non-Patent Literature 2 discloses a method for intravenously administering an F-18 labeling fluorodeoxyglucose (FDG), which has been successfully used in positron emission tomography (PET) test so far, and detecting lymph node metastasis on the basis of how much FDG has been taken into the lymph node. Purposes of this method are to minimize a resection range and to reduce the invasiveness of the surgery.

CITATION LIST

Non-Patent Literature

Non-Patent Literature
Yokoyama KUNIHIKO, Toshinami NORIHISA, Tsugawa KOUICHIROU, Miwa KOUICHI, "Senchinel rimpasetsu no aisotopu kensyutsu hou (Isotope detection method in sentinel lymph node)", Japanese-Deutsche Medizinische Berichte, vol. 46, no. 2, pp. 212-217, 2001.
Non-Patent Literature 2
Douglas A. Murrey, Jr., et al., "Perioperative 18F-fluorodeoxyglucose-guided imaging using the becquerel as a quantitative measure for optimizing surgical resection in patients with advanced malignancy," The American Journal of Surgery, 198, pp. 834-840, 2009.

SUMMARY OF INVENTION

Technical Problem

However, with the gamma camera disclosed in Non-Patent Literature 1, an image of a distribution of detected radiation is indicated on a display that is separated from the gamma camera, and therefore it is difficult to acknowledge a positional relation between the displayed image and the surgical position. Further, the technique disclosed in Non-Patent Literature 2 is not related to a method for immediately transmitting, to a surgical operator (operator), how much FDG has been taken into the lymph node. Conventionally, a method has been developed that uses, as a radiation detector to be used during a surgery, a gamma probe, a tweezer-type PET, a drop-in-type detector, an intracorporeal insertion type detector, and an extracorporeal detector in combination. However, all of them are configured to indicate, on a display of the radiation instrument, an image of a nuclide distribution and/or a radioactivity value. Thus, with any of them, an operator must move his/her point of view each time of measurement. This arises a problem of difficulty in correctly recognizing a position of an affected site on the basis of the measured radioactivity. For example, in endoscopic surgeries and robot-assisted surgeries, it is required to enable an operator to correctly identify a position of an affected site in a camera image that is to be seen by the operator.

An aspect of the present invention has an object to provide a radiation detector that can allow an operator to more correctly identify a position of a body tissue into which radionuclides have been taken.

Solution to Problem

In order to attain the above object, a radiation detector in accordance with an aspect of the present invention includes: at least one probe which has a radiation detection element housed therein and which is insertable into a body; a reporting part provided to the at least one probe; and a control part configured to cause the reporting part to operate in accordance with a result of detection of radiation, the detection being made by the radiation detection element.

A radiation detector in accordance with an aspect of the present invention is a radiation detector configured as a grasping forceps for a surgery, the grasping forceps being insertable into a body, the grasping forceps having two distal ends respectively configured as two probes each having a radiation detection element housed therein, the radiation detector including: a reporting part provided to the grasping forceps; and a control part configured to cause the reporting part to operate in accordance with a result of detection of annihilation gamma rays, the detection being made by concurrent counting carried out by the radiation detection elements respectively housed in the two probes.

Advantageous Effects of Invention

In accordance with an aspect of the present invention, it is possible to provide a radiation detector that can allow an operator to more correctly identify a position of a body tissue into which radionuclides have been taken.

Figure 12:
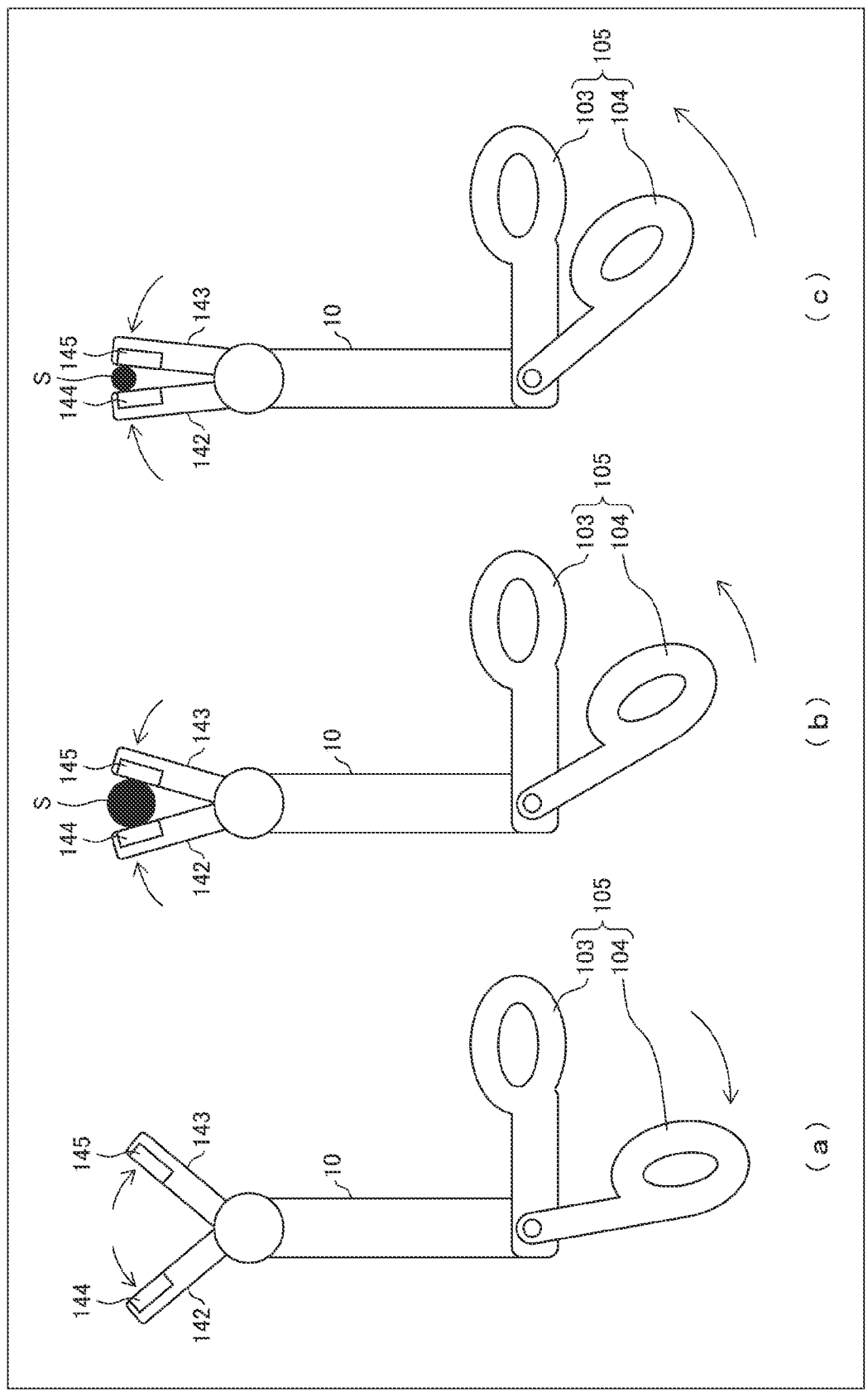

(a), (b), and (c) of FIG. 12 are views each illustrating a relation between an opening angle of a pinching part of the radiation detector in accordance with Embodiment 3 and a size of a target.

Figure 13:
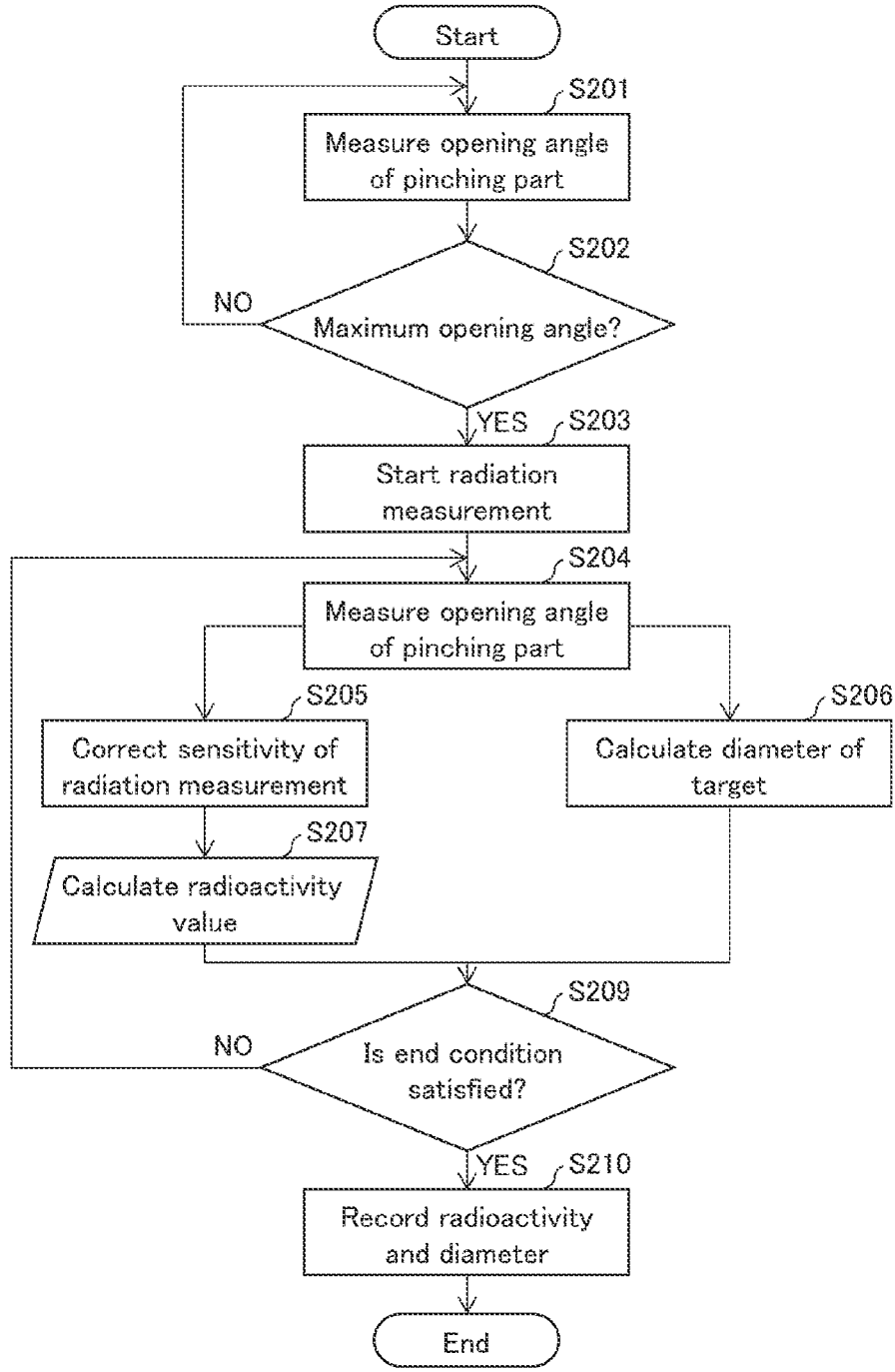

FIG. 13 is a flowchart illustrating control for starting and ending radiation measurement of the radiation detector in accordance with Embodiment 3.

Figure 14:
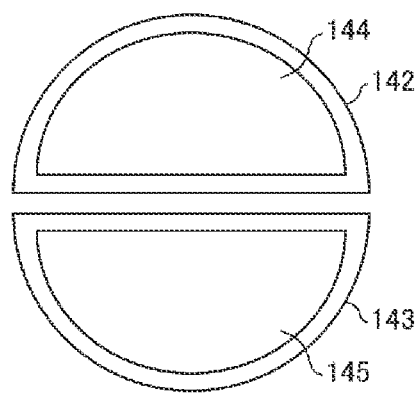

FIG. 14 is a cross-section view of a scintillator in a radiation detector in accordance with Embodiment 4.

Figure 15:
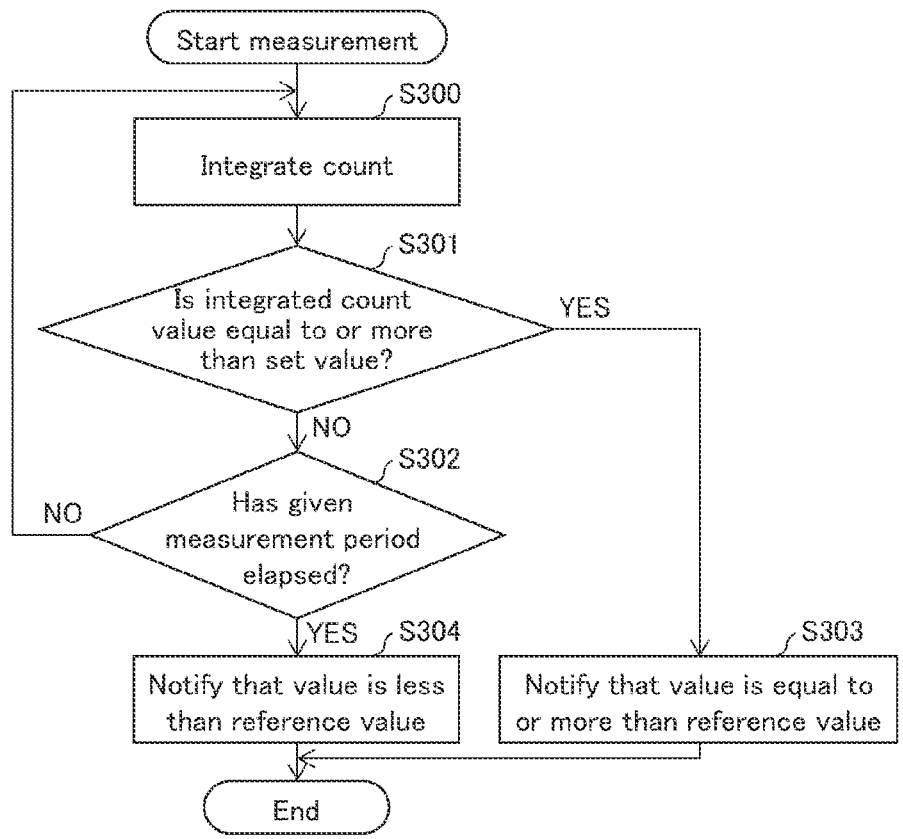

FIG. 15 is a flowchart of a measurement method to be carried out by a control part of a radiation detector in accordance with Embodiment 5.

FIG. 16 is a flowchart illustrating a measurement method in accordance with a variation of Embodiment 5.

DESCRIPTION OF EMBODIMENTS

Embodiment 1

Figure 1:
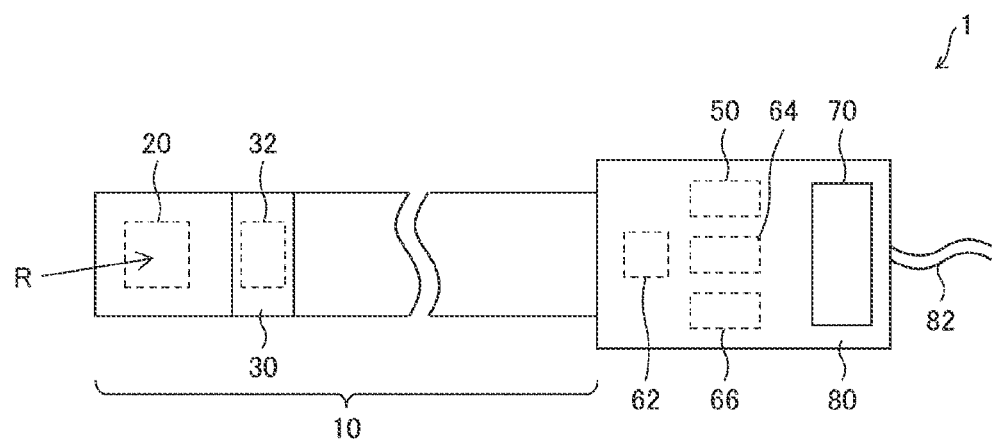
FIG. 1 is a view illustrating an overall configuration of a radiation detector in accordance with Embodiment 1 of the present invention.
Figure 2:
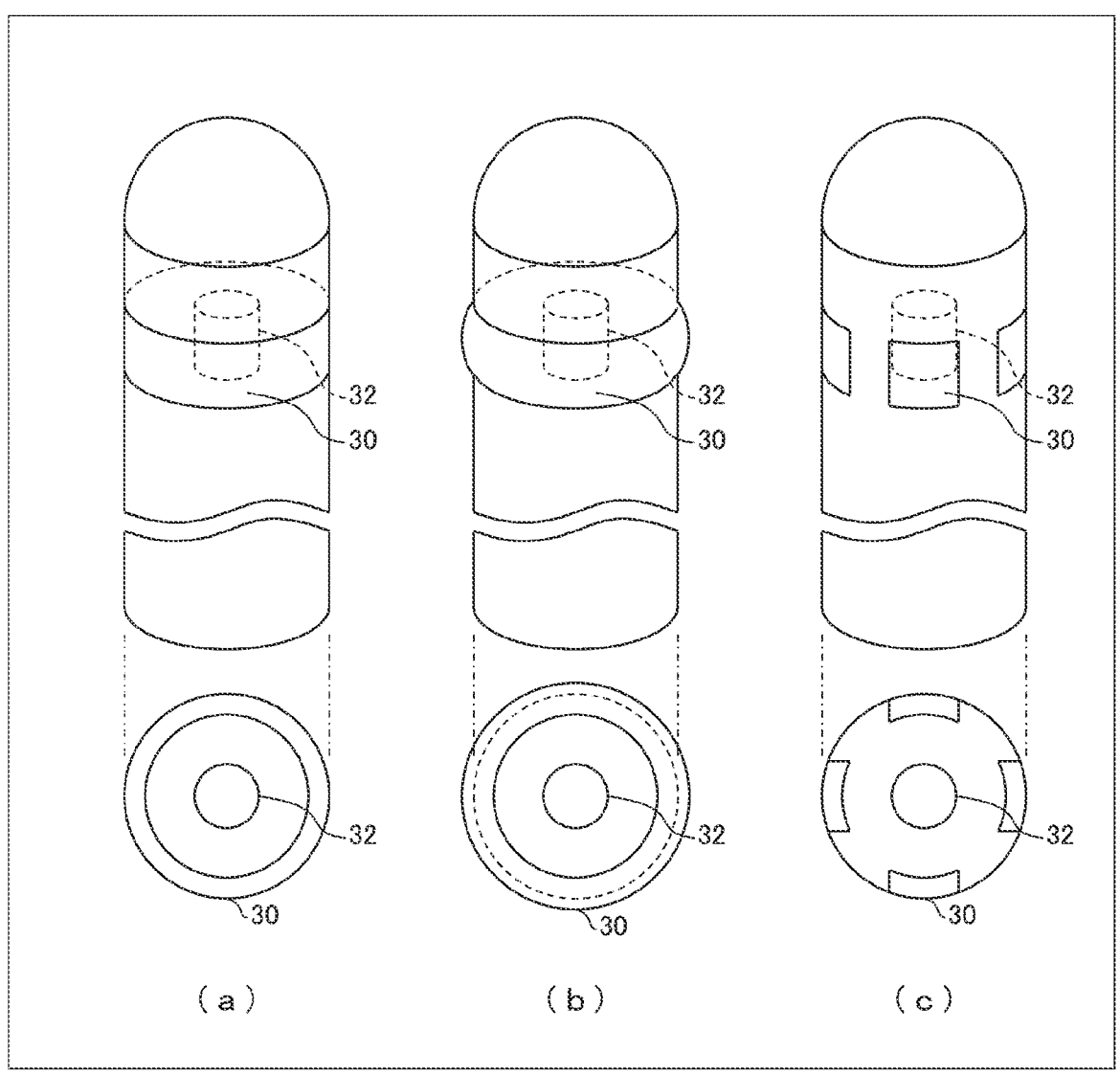
FIG. 2 illustrates exemplary forms of a light emitting part in accordance with Embodiment 1. Specifically, (a) of FIG. 2 illustrates an exemplary form of a light emitting part disposed continuously so as to surround an outer peripheral surface of a probe, and (b) of FIG. 2 illustrates an exemplary form of a light emitting part at least partially protruding from an outer surface of a probe. Further, (c) of FIG. 2 illustrates an exemplary form of light emitting parts disposed at respective of a plurality of positions on an outer surface of a probe.
Figure 3:
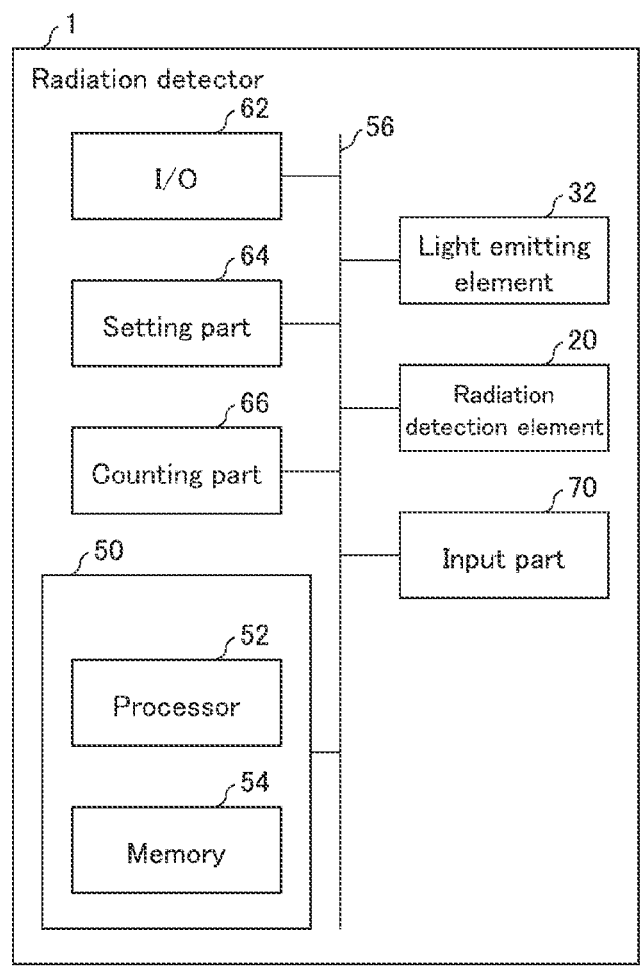
FIG. 3 is a block diagram illustrating control functions of the radiation detector in accordance with Embodiment 1.

The following description will discuss Embodiment 1 of the present invention with reference to the drawings. FIG. 1 is a view illustrating an overall configuration of a radiation detector 1 for medical use in accordance with Embodiment 1 of the present invention. FIG. 2 illustrates exemplary forms of a light emitting part in accordance with Embodiment 1. FIG. 2 includes perspective views of probes each provided with a light emitting part and cross-section views of the probes taken along their radial directions. FIG. 3 is a functional block diagram of the radiation detector 1 in accordance with Embodiment 1. The radiation detector 1 detects radiation R from radionuclides accumulated in an affected site. Then, if a measured value (count number) of the radiation R satisfies a given condition, the radiation detector 1 gives an operator (surgical operator) a report reporting that.

Configuration of Radiation Detector 1

As shown in FIG. 1, the radiation detector 1 includes a probe 10 insertable into a body and an operation part 80. The probe 10 has a radiation detection element 20 housed therein, and is provided with a light emitting part (reporting part) 30. Operation of the light emitting part 30 means light emission of the light emitting part 30. The light emitting part 30 is an example of the reporting part. In the operation part 80, a control part 50, an input-output interface (I/O) 62, a setting part 64, and a counting part 66 are arranged. The operation part 80 is further provided with an input part 70.

The radiation detection element 20 is disposed at a distal end of the probe 10. The operator can make the distal end of the probe 10 closer to an affected site to check how much radiation R is detected. The type of the radiation detection element 20 is not limited to any particular one. Preferably, the radiation detection element 20 is a small detection element such a semiconductor detection element or a scintillation detection element. Usable as the semiconductor detection element is a CdTe (CZT) semiconductor detection element, a Si semiconductor detection element, a Ge semiconductor detection element, or the like. Usable as the scintillation detection element is a CsI (Tl) scintillator, a NaI (Tl) scintillator, or the like. The radiation detection element 20 converts an energy of the radiation R into an electric signal and output the electric signal. A configuration for converting a radiation energy into an electric signal may be a known configuration.

As a method for identifying an incident direction of the radiation R that is to be detected by the radiation detection element 20, a collimator system, a Compton camera system, a concurrent counting system, or the like can be selected. The collimator system employs a collimator that regulates the incident direction of the radiation R that enters the radiation detection element 20. On the basis of the position of the radiation detection element 20 that has detected the radiation R, it is possible to determine the incident direction of the radiation R that has entered the collimator. The Compton camera system employs a radiation detection element 20 for a Compton camera that includes a scatterer and an absorber. Then, on the basis of a position in the scatterer where scattering occurs and a position in the absorber where absorption occurs, it is possible to determine an incident direction of a gamma ray. The concurrent counting system employs two radiation detection elements 20 arranged to face each other. Then, only when concurrent counting by the two radiation detection elements 20 is carried out, radiation is counted and it is possible to determine that a radiation source is present between the two radiation detection elements 20. The concurrent counting system is targeted at a proton discharging nuclide.

The light emitting part 30 is disposed at the distal end of the probe 10. The light emitting part 30 is disposed near the radiation detection element 20. The light emitting part 30 functions to, if the radiation detection element 20 detects radiation R satisfying a given condition, give the operator a report reporting that. The operator makes the distal end of the probe 10 closer to the affected site to determine whether or not the radiation R is detected. For this, in order to allow the operator to recognize light emission of the light emitting part 30 even without moving his/her sightline while operating the probe 10, the light emitting part 30 is disposed at the distal end of the probe 10.

The light emitting part 30 is provided on an outer surface of the probe 10. To be more specific, the light emitting part 30 is disposed continuously so as to surround the outer peripheral surface of the probe 10, as shown in (a) of FIG. 2. However, the shape of the light emitting part 30 is not limited to this. In the example shown in (a) of FIG. 2, the light emitting part 30 surrounds the probe 10 so as to have the same height as that of the outer peripheral surface of the probe 10. Alternatively, as shown in (b) of FIG. 2, the light emitting part 30 may at least partially protrude from the outer surface of the probe 10. Further alternatively, as shown in (c) of FIG. 2, the light emitting part 30 may include a plurality of light emitting parts 30 disposed at respective of a plurality of positions on the outer surface of the probe 10. With any of these configurations, the operator can reliably recognize light emission of the light emitting part 30 even when the orientation of the probe 10 changes.

The light emitting part 30 is constituted by, e.g., a light-guiding material that guides light therethrough, and guides light from a light emitting element 32, which is housed therein, so that the light is discharged to the outside. The light emitting element 32 is, for example, a light emitting diode (LED). The number of the light emitting elements 31 may be one or two or more.

The input part 70 is provided on an outer surface of the operation part 80. The input part 70 is, for example, a touch panel-type liquid crystal display via which a threshold of the number of times of detection of radiation R that causes light emission of the light emitting part 30 can be entered. A cable 82 is a power supply cable that supplies electric power to the radiation detector 1. The cable 82 may also function as a cable via which the radiation detector 1 communicates with the outside. Note that the cable 82 may be omitted when the radiation detector 1 is configured to include a power source therein.

Control of Radiation Detector 1

FIG. 3 is a functional block diagram related to control of the radiation detector 1 in accordance with Embodiment 1. The control part 50 controls the whole of the radiation detector 1. The control part 50 includes a processor 52 and a memory 54. The memory 54 is constituted by, e.g., a volatile random access memory (RAM) and a nonvolatile read only memory (ROM), and stores various control programs and data therein. The memory 54 may store, as setting values, a threshold of a measured value of radiation that causes the light emitting part 30 to emit light, a light emission period, and/or the like. The processor 52 is, for example, a central processing unit (CPU) or a micro processing unit (MPU). The processor 52 reads out various control programs from the ROM and loads the programs onto the RAM. Then, the processor 52 executes the programs to realize the setting part 64 and the counting part 66. Alternatively, the processor 52 may be a dedicated processor, such as an application specific integrated circuit (ASIC) or a field programmable gate array (FPGA). The radiation detection element 20, the light emitting element 32, the control part 50, the I/O 62, the setting part 64, the counting part 66, and the input part 70 are electrically connected to each other via a bus 56.

The input-output interface (I/O) 62 transmits and receives signals and information from and to the outside. The setting part 64 obtains a threshold entered by the operator, and sets the threshold with respect to the control part 50. The threshold is a threshold that is used to determine whether to cause the light emitting part 30 to emit light and that corresponds to a result of detection of radiation. Specifically, the setting part 64 obtains, via the I/O 62, information regarding the threshold entered by the operator via the input part 70, for example. The setting part 64 stores, in the memory 54 or setting register, the information regarding the obtained threshold, so as to set the threshold entered by the operator with respect to the control part 50. The counting part 66 obtains the electric signal output by the radiation detection element 20. The counting part 66 counts the number of times of detection of the radiation, and outputs the counting result to the control part 50.

The control part 50 causes the light emitting part 30 to emit light in accordance with the radiation detection result given by the radiation detection element 20. For example, the control part 50 causes the light emitting part 30 to emit light each time the counting part 66 counts radiation. Alternatively, the control part 50 may carry out control for causing the light emitting element 32 to emit light for a given period of time if the number of times of detection of radiation, obtained from the counting part 66, is greater than the threshold. If the period of time in which light is emitted is too long, it is impossible to discriminate individual detections of radiation from one another. Meanwhile, if the period of time for causing light emission is too short, it may be impossible to recognize the light emission. Thus, it is preferable to set an appropriate light emission period in advance. Alternatively, the operator may set, via the input part 70, a light emission period in accordance with the measurement condition.

Figure 4:
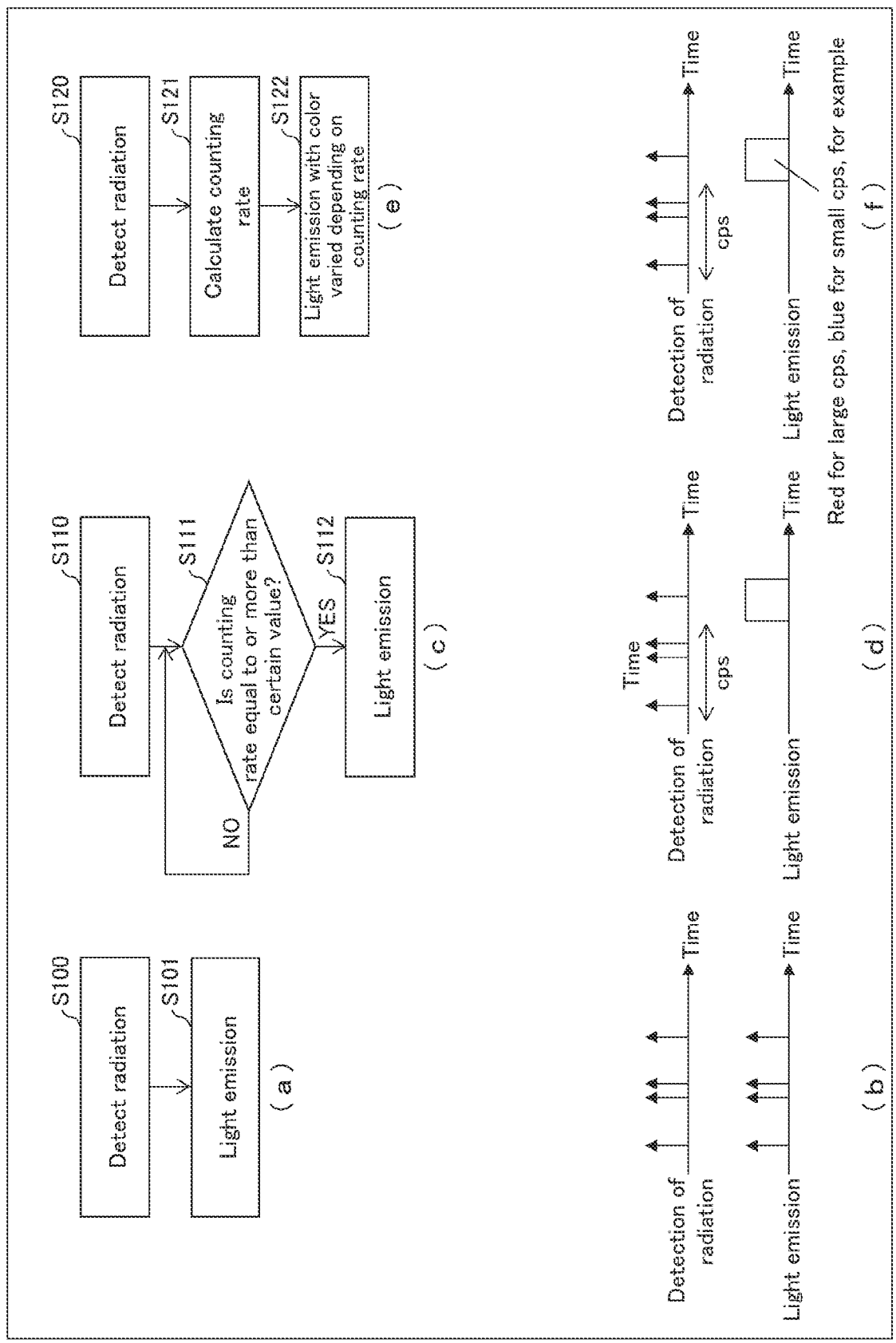
FIG. 4 is a view including flowchart examples of light emission control of the radiation detector in accordance with Embodiment 1. Specifically, (a), (c), and (e) of FIG. 4 respectively indicate first, second, and third flowchart examples. (b), (d), and (f) of FIG. 4 are views each illustrating an example of a result of detection of radiation and an example of a light emission timing that correspond to a respective one of these flowchart examples.

The following description will discuss, with reference to FIG. 4, a control method for causing the light emitting part 30 to emit light. For example, as shown in a first flowchart example in (a) of FIG. 4 and (b) of FIG. 4, each time the counting part 66 counts radiation (step S100), the control part 50 causes the light emitting element 32 to emit light for a given period of time once (step S101). This is an example in which light emission is carried out regardless of a counting rate of the radiation. In this case, by referring to the frequency of light emission, the operator determines whether or not the position of the probe 10 is close to an affected site (radiation source) in which radionuclides are accumulated. If the frequency of light emission is high, the operator can determine that the position of the probe 10 is close to the affected site. By checking the frequency of light emission while changing the position of the probe 10, the operator can determine that the affected site is present in the position having a high light emission frequency.

Alternatively, the control part 50 may carry out control for causing the light emitting part 30 to emit light if the counting rate of the radiation is equal to or more than a given value. The counting rate is represented by, e.g., a count per second (cps), which is the number of times of detection per second. As shown in a second flowchart example in (c) of FIG. 4 and (d) of FIG. 4, the counting part 66 calculates the counting rate by (i) integrating the number of times of detection of radiation for a given period of time (e.g., several seconds to several tens of seconds) and (ii) dividing the resulting value by the given period of time (step S110). Then, the control part 50 determines whether or not the counting rate calculated by the counting part 66 is equal to or more than a given counting rate (threshold) (step S111). If the counting rate is equal to or more than the given threshold (step S111: YES), the control part 50 causes the light emitting part 30 to emit light for a given period of time (step S112). If the counting rate is not equal to or more than the given threshold (step S111: NO), the control part 50 returns to step S111 without causing the light emitting part 30 to emit light, and determines whether or not a counting rate obtained for a given period of time slightly shifted from the previous one is equal to or more than the given counting rate. If light emission is present, the operator can determine the position of the probe 10 is close to the affected site.

For another example, the control part 50 may control the light emitting part 30 so that a light emission mode is changed in accordance with the count or counting rate of radiation. As shown in a third flowchart example in (e) of FIG. 4 and (f) of FIG. 4, the counting part 66 counts the number of rays of detected radiation for a given period of time (e.g., several seconds to several tens of seconds) (step S120), and calculates the counting rate (step S121). Then, the control part 50 causes the light emitting part 30 to emit light in a given mode in accordance with the counting rate (step S122). For example, the control part 50 does not cause the light emitting element 32 to emit light, if the counting rate is less than a first threshold; the control part 50 causes the light emitting element 32 to emit blue light, if the counting rate is equal to or more than the first threshold and less than a second threshold; the control part 50 causes the light emitting element 32 to emit red light, if the counting rate is equal to or more than the second threshold. When red light is emitted, the operator can determine that the position of the probe 10 is close to the affected site or that an amount of radionuclides accumulated in the affected site is large. Further, the control part 50 may carry out control for changing the intensity (luminance) of light emitted from the light emitting part 30, in accordance with the counting rate. The operator can determine that the position of the probe 10 is close to the affected site or that an amount of radionuclides accumulated in the affected site is large, as the intensity of emitted light is higher (brighter). Moreover, the control part 50 may carry out control for changing the light emission pattern or the light emission period of the light emitting part 30 in accordance with the counting rate.

The above-discussed threshold is preferably determined by the operator as appropriate in accordance with, e.g., (i) a type of a radionuclide, (ii) an amount of administered radionuclides, (iii) an amount of accumulated radionuclides (a size of an affected site), and/or (iv) a period of time taken from the administering to the measurement.

Example of Use of Radiation Detector 1

Figure 5:
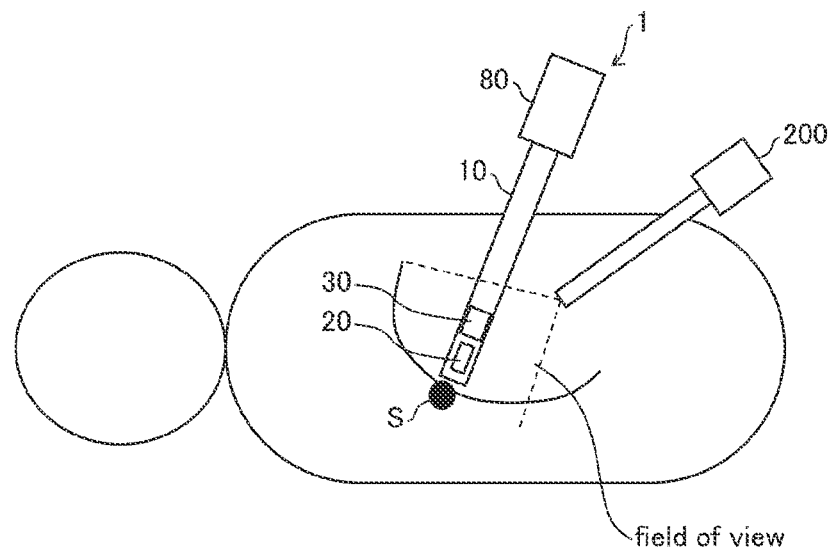
FIG. 5 is a view schematically illustrating an example of use of the radiation detector in accordance with Embodiment 1.

As shown in FIG. 5, the radiation detector 1 can be used by being inserted into the body of a patient via a trocar in an endoscopic surgery or a robot-assisted surgery. While seeing an image of an optical camera 200, the operator carries out radiation measurement by making the radiation detection element 20 of the probe 10 closer to a tissue S (e.g., a lymph node) in order to determine whether or not a medicament containing radionuclides is accumulated in the tissue S. The determination of whether or not certain radiation is detected can be made in a field of view of the optical camera 200 in accordance with light emission, flashing, color tone, and/or the like of the light emitting part 30. Thus, the operator can acknowledge, in real time, a result of the radiation measurement via the optical camera 200.

As discussed above, the radiation detector 1 in accordance with Embodiment 1 measures, with the radiation detection element 20 of the probe 10, radiation from the radionuclides taken into a body tissue (affected site), and causes the light emitting part 30, disposed at the distal end of the probe, to emit light as appropriate. The operator can easily recognize light emission of the light emitting part 30 disposed at the distal end of the probe 10, even without changing his/her sightline so as to be shifted from the probe 10. That is, the operator does not need to see another display screen or the like that is not a display screen showing an image of a part adjacent to the distal end of the probe 10 (i.e., a part around the affected site), for example, another display screen indicating a radioactivity value. Consequently, the operator can more correctly identify the position of the body tissue.

Variations

The above-discussed Embodiment 1 employs the light emitting part 30 in order to give the operator a report reporting that radiation has been detected. However, the reporting method is not limited to the light emitting part 30. For example, the light emitting part 30 may be replaced with a speaker that emits a detection sound. In a case where the speaker is employed, the speaker may not be disposed on the outer surface of the probe 10, but may be housed in the probe 10. However, it is preferable to position the speaker at a location close to the distal end of the probe 10, from the viewpoint of giving a report to the operator. The detection sound may be emitted each time radiation is detected. The mode (e.g., frequency, tone) of the detection sound may be changed in accordance with the counting rate, so as to give the operator a report reporting a level of the counting rate.

Figure 6:
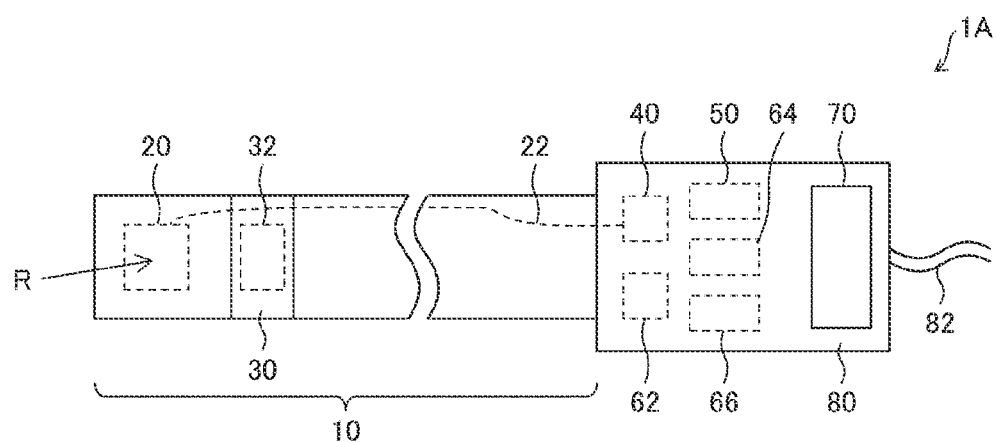
FIG. 6 is a view illustrating an overall configuration of a radiation detector including a scintillation detection element.
Figure 7:
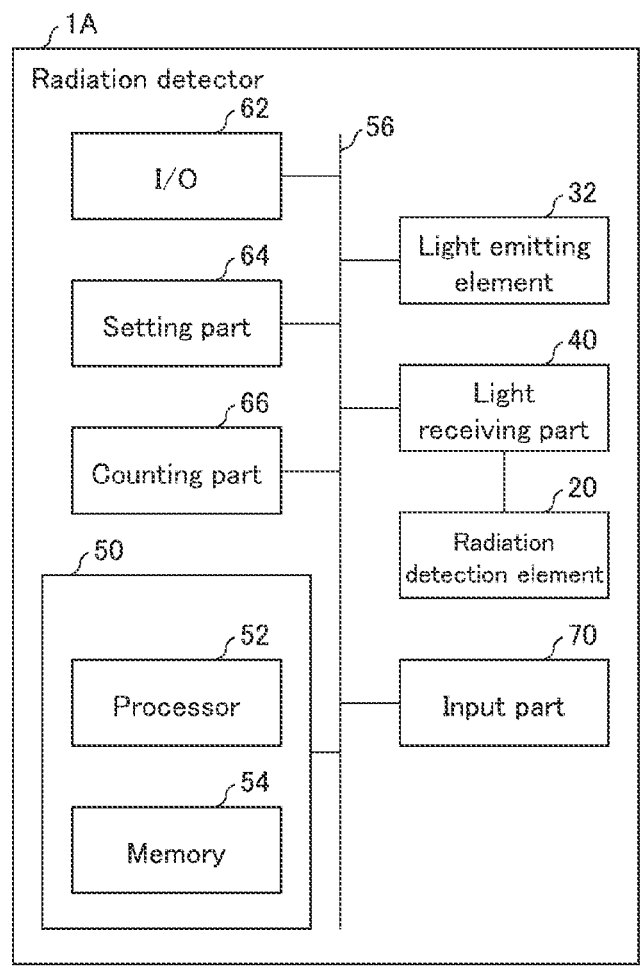
FIG. 7 is a block diagram illustrating control functions of the radiation detector including the scintillation detection element.

As the radiation detection element 20, a scintillation element may be used. As shown in FIGS. 6 and 7, a radiation detector 1A includes a radiation detection element 20, which is a scintillation detection element, and a light receiving part (amplifying part) 40. The light receiving part 40 is connected to the radiation detection element 40 via an optical fiber 22. The optical fiber 22 guides, to the light receiving part 40, scintillation light generated in the radiation detection element 20. The light receiving part 40 receives and amplifies the scintillation light transmitted thereto from the radiation detection element 20 via the optical fiber 22, and outputs the resultant as an electric signal to the counting part 66. The light receiving part 40 is, for example, a silicon photomultiplier. The light receiving part 40 requires a relatively high voltage, e.g., approximately 70 volts. Therefore, for safety, the light receiving part 40 is preferably disposed inside the operation part 80, rather than in the probe 10 that is to be inserted into a body.

In accordance with Embodiment 1 and the variation discussed above, the light emitting element 30 includes, in its inside, the light emitting element 32. However, this is not limitative. Alternatively, the light emitting part 30 and the light emitting element 32 may be disposed so as to be spaced from each other (see FIG. 8, which will be discussed later). In this case, the light emitting part 30 and the light emitting element 32 may be connected with each other via an optical fiber. This can further reduce the size of the probe 10.

In Embodiment 1 discussed above, the control part 50 is housed in the operation part 80 of the radiation detector 1. Alternatively, the control part 50 may be disposed in another housing that is not the probe 10 or the operation part 80 of the radiation detector 1. In this case, as exemplified in FIG. 3, the control part 50 is disposed in the another housing in a state where the control part 50 is electrically connected, via the bus 56, to the I/O 62, the setting part 64, the counting part 66, the radiation detection element 20, the light emitting element 32, and the input part 70.

Embodiment 2

Figure 8:
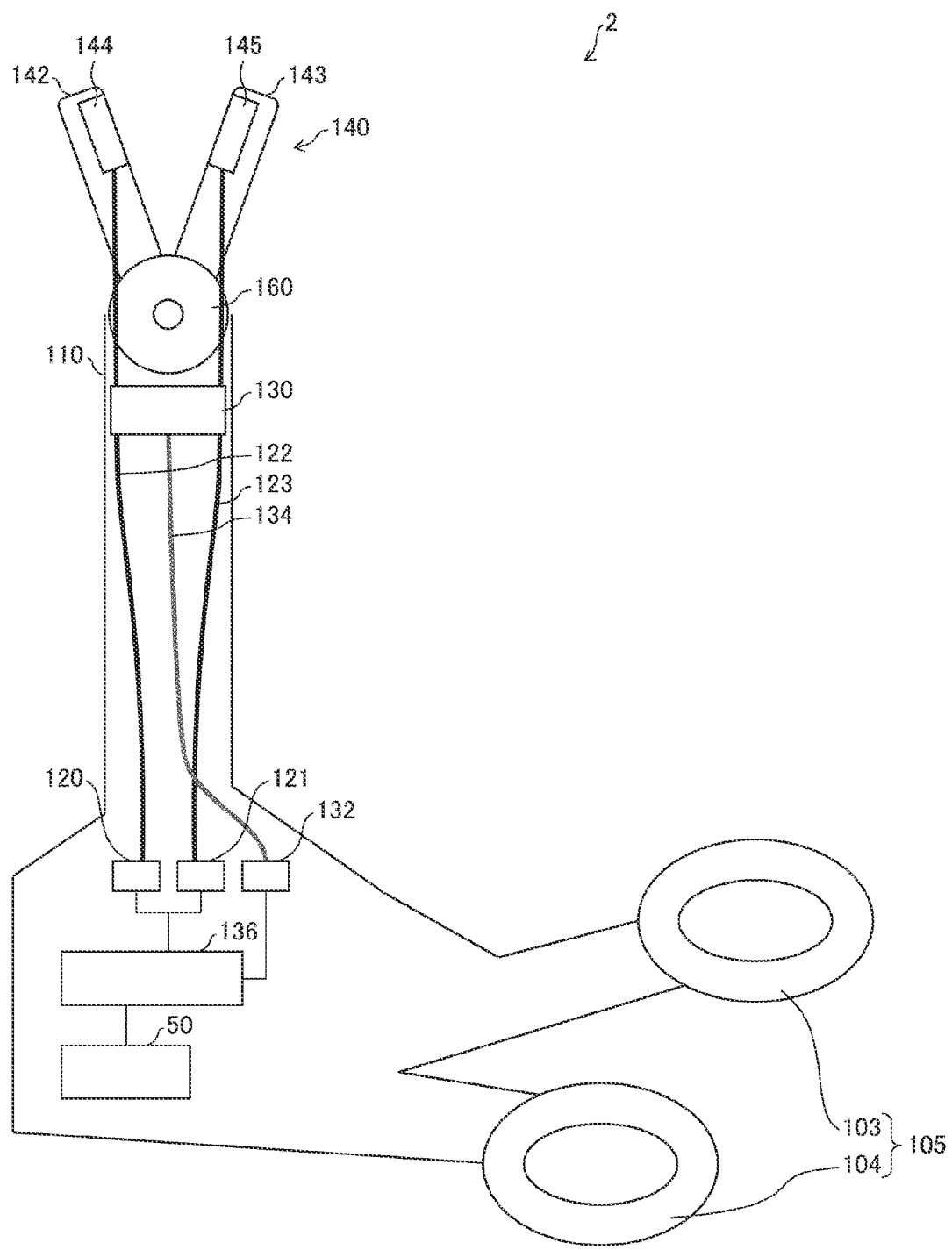
FIG. 8 is a view schematically illustrating a configuration of a radiation detector in accordance with Embodiment 2, which is configured as a grasping forceps for a surgery.

Next, the following description will discuss Embodiment 2 with reference to the drawings. Note that members having identical configurations or functions to those of Embodiment 1 are given identical reference signs, and their descriptions will be omitted. FIG. 8 is a view schematically illustrating a configuration of a radiation detector 2 in accordance with Embodiment 2, which is configured as a grasping forceps for a surgery. The grasping forceps is a surgical instrument including two pinching parts that are in the shape of scissors and that are configured to pinch and hold a body tissue. In the radiation detector 2, the two pinching parts (probe) have a pair of radiation detection elements housed therein. The radiation detector 2 measures radioactivity of a target while pinching the target with the radiation detection elements.

Configuration of Radiation Detector 2

As shown in FIG. 8, the radiation detector 2 includes a main body 110, an operation part 105 disposed on one end side of the main body 110, and a pinching part 140 disposed on the other end side of the main body 110. The main body 110 has a first light receiving element (amplifying part) 120, a second light receiving element (amplifying part) 121, a light emitting element 132, a concurrent count circuit 136, and a control part 50, which are housed in the main body 110. Each of the first light receiving element 120 and the second light receiving element 121 is, for example, a silicon photomultiplier, and requires a relatively high voltage of approximately 70 volts. Therefore, for safety, the first light receiving element 120 and the second light receiving element 121 are preferably disposed at a location that is separated as much as possible from the pinching part 140 and that is close to the operation part 105. Note that the radiation detector 2 may include an input part and a setting part (not illustrated). The input part and the setting part of the radiation detector 2 have the same functions as those of the input part 70 and the setting part 64 discussed in Embodiment 1, for example.

The operation part 105 is a mechanism part that causes an opening/closing motion of the pinching part 140. The operation part 105 includes a first operation part 103 in which, e.g., a finger other than a thumb can be caught and a second operation part 104 in which, e.g., a thumb can be caught. Opening and closing of the first operation part 103 and the second operation part 104 can be carried out by a single hand.

The pinching part 140 includes a first pinching part 142 and a second pinching part 143. Each of the first pinching part 142 and the second pinching part 143 corresponds to the probe 10 in Embodiment 1. The first pinching part 142 is provided with a first scintillator (radiation detection element) 144. The second pinching part 143 is provided with a second scintillator (radiation detection element) 145. The first scintillator 144 and the first light receiving element 120 are optically coupled to each other via a first optical fiber 122. The second scintillator 145 and the second light receiving element 121 are optically coupled to each other via a second optical fiber 123.

The first pinching part 142 and the second pinching part 143 carry out an opening/closing motion in which the first pinching part 142 and the second pinching part 143 sway in opposite directions centered around an opening/closing shaft 160 disposed on the second end side of the main body 110. The opening/closing motion of the first operation part 103 and the second operation part 104 is transmitted via a transmission mechanism (not illustrated) in the main body 110, and is then converted into an opening/closing motion of the first pinching part 142 and the second pinching part 143.

A light emitting part 130 is provided in the vicinity of the opening/closing shaft 160 of the main body 110. The light emitting part 130 emits light upon reception of light from the light emitting element 132. The light emitting part 130 and the light emitting element 132 are disposed so as to be spaced from each other. The light emitting part 130 and light emitting element 132 are optically coupled to each other via an optical fiber 134. The light emitting part 130 is constituted by, for example, a light diffusing material. The light emitting part 130, which is disposed in the vicinity of the opening/closing shaft 130 in Embodiment 2, is preferably disposed so as to be close as much as possible to the pinching part 140 of the main body 110. More preferably, the light emitting part 130 is provided at least either of the first pinching part 142 and the second pinching part 143 of the pinching part 140.

Operation of Radiation Detector 2

An operator pinches a tissue of the affected site with the first pinching part 142 and the second pinching part 143 of the radiation detector 2, and carries out radiation measurement. The operator administers an F-18 labeling fluorodeoxyglucose (FDG) to a patient in advance. The F-18 labeling FDG is likely to be taken into a cancer tissue and accumulated therein. The F-18 discharges two annihilation gamma rays generated by annihilation of the set of a positron and an electron caused by positron decay. The two annihilation gamma rays have an identical energy of 511 (KeV), and are concurrently generated in directions oriented 180 degrees with respect to each other. Thus, the two annihilation gamma rays are concurrently detected by the first scintillator 144 and the second scintillator 145 disposed opposite to each other. Rays of radiation not detected concurrently are not the ones derived from the annihilation gamma rays. Otherwise, even if the rays of the radiation are annihilation gamma rays, the rays of the radiation are the ones incident from the outside of a field of view. Therefore, the rays of the radiation can be regarded as background radiation, and can be eliminated. Thus, there is no need to consider shielding, etc. Consequently, the radiation detector 2 having a simple configuration can be achieved.

Scintillation light generated in the first optical fiber 144 due to the radiation of 511 (KeV) is transmitted to the first light receiving element 120 via the first optical fiber 122. The first light receiving element 120 converts the scintillation light into an electric signal and outputs the electric signal to the concurrent count circuit 136. Scintillation light generated in the second scintillator 145 due to the radiation of 511 (KeV) is transmitted to the second light receiving element 121 via the second optical fiber 123. The second light receiving element 121 converts the scintillation light into an electric signal and outputs the electric signal to the concurrent count circuit 136. If both the electric signal from the first scintillator 144 and the electric signal from the second scintillator 145 are the ones generated due to the radiation of 511 (KeV) and are detected concurrently, the concurrent count circuit 136 determines that the annihilation gamma rays have been detected, and outputs a detection signal to the control part 50. The expression "concurrently" herein means that a difference between the arrival times is smaller than several nanoseconds or several tens of nanoseconds. If the detection signal from the concurrent count circuit 136 satisfies a given condition, the control part 50 causes the light emitting part 130 to emit light.

Figure 9:
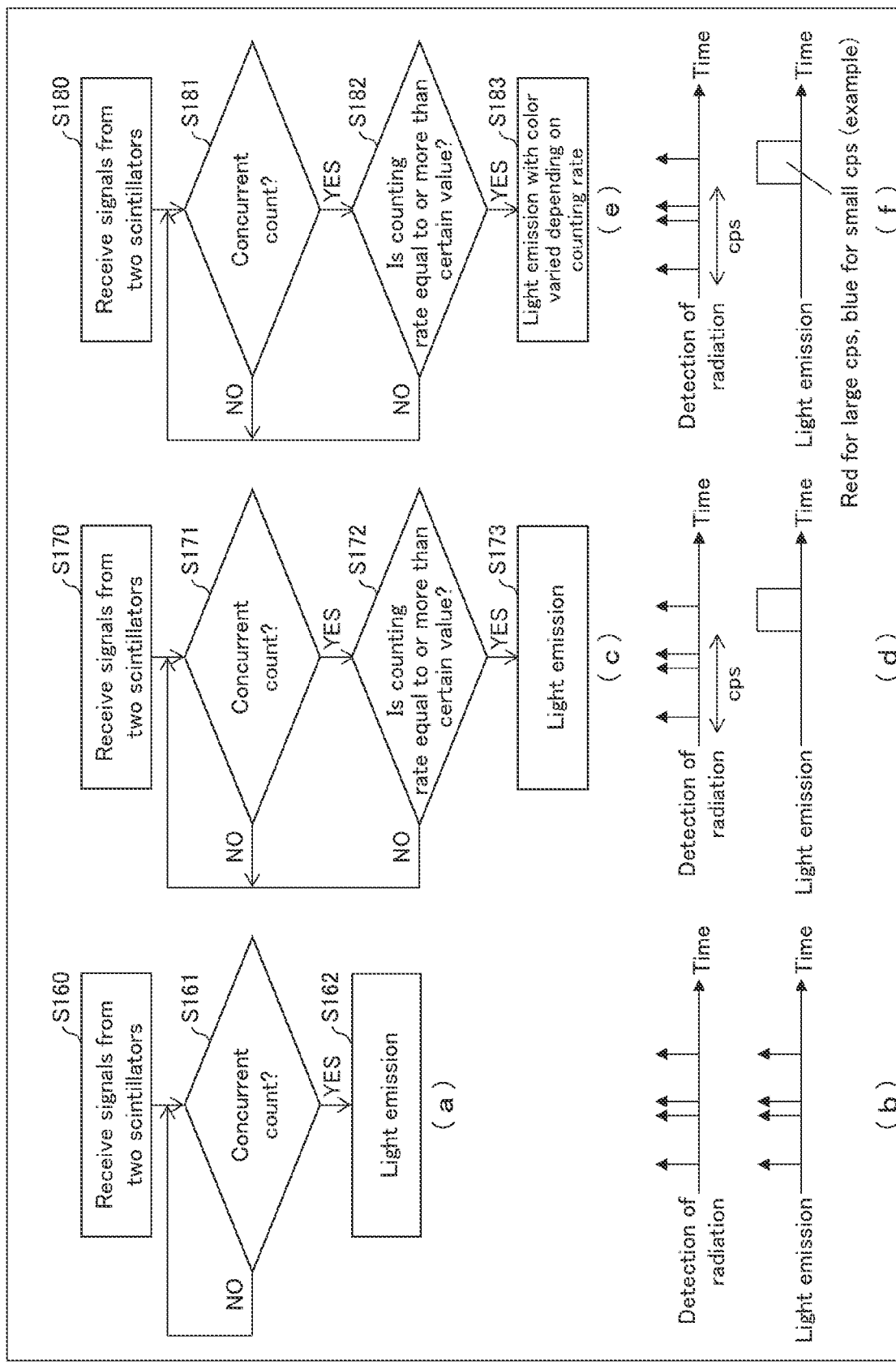
FIG. 9 is a view including flowchart examples of light emission control of the radiation detector in accordance with Embodiment 2. Specifically, (a), (c), and (e) of FIG. 9 respectively indicate fourth, fifth, and sixth flowchart examples. (b), (d), and (f) of FIG. 9 are views each illustrating an example of a result of detection of radiation and an example of a light emission timing that correspond to a respective one of these flowchart examples.

The following description will discuss a control method carried out by the control part 50 to cause the light emitting part 130 to emit light. Firstly discussed is a control method for causing light emission each time annihilation gamma rays are detected. As shown in a fourth flowchart example in (a) of FIG. 9 and (b) of FIG. 9, the concurrent count circuit 136 receives, via the first light receiving element 120 and the second light receiving element 121, electric signals (detection signals) of rays of radiation detected by the first scintillator 144 and the second scintillator 145, respectively (step S160). Next, the concurrent count circuit 136 determines whether or not the detection signals from the first scintillator 144 and the second scintillator 145 are concurrently received (step S161). If two detection signals are concurrently detected in step S161 (step S161: YES), it is possible to determine that annihilation gamma rays are detected. Thus, the concurrent count circuit 136 outputs, to the control part 50, a signal indicating that the radiation is detected. If two detection signals are not received concurrently (step S161: NO), the process to be carried out by the control part 50 returns to a part before step S161. Next, if the control part 50 receives, from the concurrent count circuit 136, a signal indicating that radiation is detected, the control part 50 causes the light emitting element 132 to emit light (step S162). The light emitted by the light emitting element 132 is transmitted via the optical fiber 134, and causes the light emitting part 130 to emit light.

Alternatively, a control method for causing light emission when a counting rate of annihilation gamma rays is equal to or more than a given threshold may be adopted. The counting rate is as discussed in Embodiment 1. As shown in a fifth flowchart example in (c) of FIG. 9 and (d) of FIG. 9, the concurrent count circuit 136 receives the detection signals of the rays of the radiation detected by the first scintillator 144 and the second scintillator 145 (step S170). Next, the concurrent count circuit 136 determines whether or not the two detection signals are concurrently received (step S171). If it is determined in step S171 that the two detection signals are concurrently received (step S171: YES), the concurrent count circuit 136 outputs, to the control part 50, a signal indicating that the radiation is detected. Next, the control part 50 determines whether or not a frequency of reception (counting rate) of a signal which is supplied from the concurrent count circuit 136 and which indicates that radiation is detected is equal to or more than a threshold (step S172). If it is determined in step S172 that the counting rate is equal to or more than the threshold (step S172: YES), the control part 50 causes the light emitting element 132 to emit light (step S173). If two detection signals are not concurrently received (step S171: NO) or the counting rate is not equal to or more than the threshold (step S172: NO), the process to be carried out by the control part 50 returns to a part before step S171. The above-described light emitted by the light emitting element 132 is transmitted via the optical fiber 134, and causes the light emitting part 130 to emit light.

Further, the control part 50 may carry out control for changing the light emission mode in accordance with the counting rate of the annihilation gamma rays. As shown in a sixth flowchart example in (e) of FIG. 9 and (f) of FIG. 9, the concurrent count circuit 136 receives the detection signals of the rays of the radiation detected by the first scintillator 144 and the second scintillator 145 (step S180). Next, the concurrent count circuit 136 determines whether or not the two detection signals are concurrently received (step S181). If it is determined in step S181 that the two detection signals are concurrently received (step S181: YES), the concurrent count circuit 136 outputs, to the control part 50, a signal indicating that the radiation is detected. Next, the control part 50 determines whether or not a frequency of reception (counting rate) of a signal which is supplied from the concurrent count circuit 136 and which indicates that radiation is detected is equal to or more than a threshold (step S182). If it is determined in step S182 that the counting rate is equal to or more than the threshold (step S182: YES), the control part 50 causes the light emitting element 132 to emit light having a given color in accordance with the counting rate (step S183). If two detection signals are not concurrently received (step S181: NO) or the counting rate is not equal to or more than the threshold (step S182: NO), the process to be carried out by the control part 50 returns to a part before step S181. For example, the control part 50 does not cause light emission, if the counting rate is less than a first threshold; the control part 50 causes the light emitting element 132 to emit blue light, if the counting rate is equal to or more than the first threshold and less than a second threshold; the control part 50 causes the light emitting element 132 to emit red light, if the counting rate is equal to or more than the second threshold. Alternatively, the control part 50 may carry out control for changing the frequency of light emission, e.g., flashing, in accordance with the counting rate. A method for setting the thresholds is as discussed in Embodiment 1.

Example of Use of Radiation Detector 2

Figure 10:
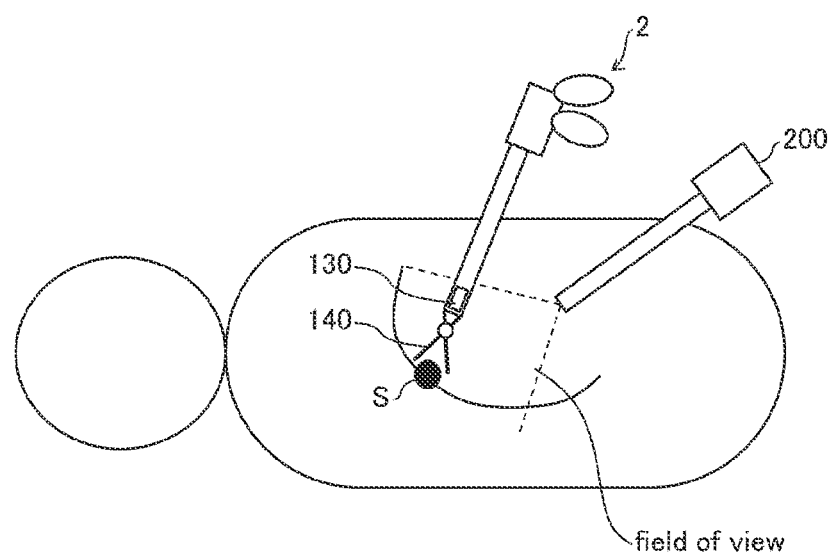
FIG. 10 is a view schematically illustrating an example of use of the radiation detector in accordance with Embodiment 2.

As shown in FIG. 10, the radiation detector 2 can be used in endoscopic surgeries and robot-assisted surgeries. While seeing an image of an optical camera 200, the operator measures radioactivity from a target by pinching the target with the two scintillators 144 and 145 of the pinching part 140 in order to determine whether or not F-18 labeling FDG is accumulated in a tissue (e.g., a lymph node) S. The determination of whether or not annihilation gamma rays are detected can be made in a field of view of the optical camera 200 in accordance with light emission, flashing, color tone, and/or the like of the light emitting part 130. Thus, the operator can acknowledge, in real time, a result of the radiation measurement via the optical camera 200.

As discussed above, by checking for light emission of the light emitting part 130, the operator can determine whether or not the F-18 labeling FDG is accumulated in a tissue pinched by the first pinching part 142 and the second pinching part 143.

The radiation detector 2 in accordance with Embodiment 2 detects only annihilation gamma rays from a tissue pinched by the pinching part 140, and therefore would not be affected by other radiation than the annihilation gamma rays. Further, the operator can easily recognize light emission of the light emitting part 130, which is disposed in the vicinity of the pinching part 140 or in the pinching part 140, even without changing his/her sightline so as to be shifted from the pinching part 140. That is, the operator can more correctly recognize that radionuclides are accumulated in the tissue pinched by the pinching part 140, without the need to see, e.g., another display screen.

Embodiment 3

Figure 11:
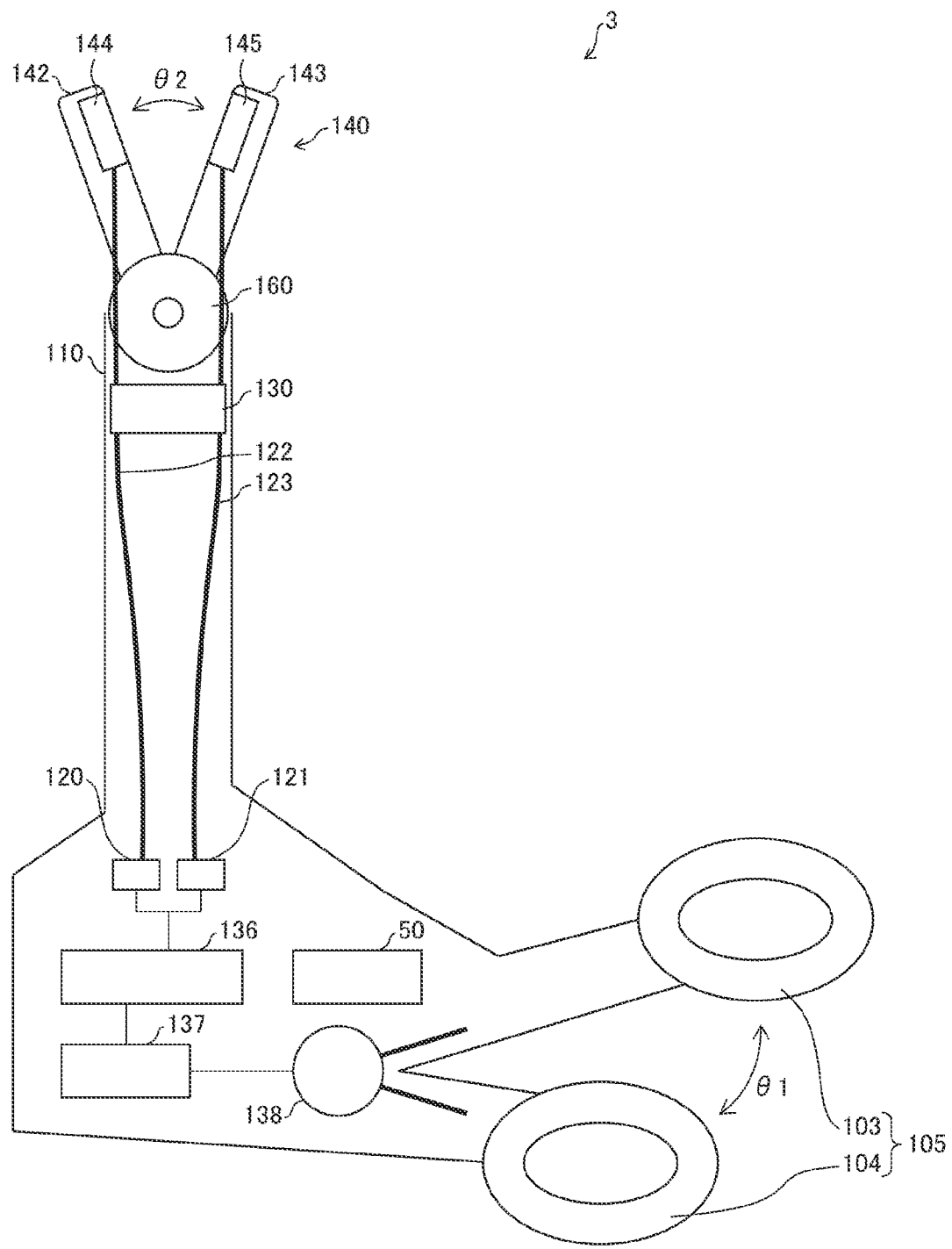
FIG. 11 is a view schematically illustrating a configuration of a radiation detector in accordance with Embodiment 3, which configured as a grasping forceps for a surgery.

Next, the following description will discuss Embodiment 3 with reference to the drawings. Note that members having identical configurations or functions to those of Embodiment 2 are given identical reference signs, and their descriptions will be omitted. FIG. 11 is a view schematically illustrating a configuration of a radiation detector 3 in accordance with Embodiment 3, which is configured as a grasping forceps for a surgery. FIG. 12 is a view illustrating a relation between an opening angle of a pinching part 140 and a size of a target.

Configuration of Radiation Detector 3

The radiation detector 3 has a substantially identical configuration to that of the radiation detector 2. Specifically, the radiation detector 3 includes a main body 110, an operation part 105, and a pinching part 140. In the main body 110, a light emitting part 130 is disposed in the vicinity of an opening/closing shaft 160, and a light emitting element 132 (not illustrated) is disposed inside the light emitting part 130. The main body 110 has a first light receiving element 120, a second light receiving element 121, a concurrent count circuit 136, a correction part 137, an encoder 138, and a control part 50, which are housed in the main body 110. Note that the radiation detector 3 may include an input part and a setting part (not illustrated).

Unlike the radiation detector 2, the radiation detector 3 includes the correction part 137 and the encoder 138. The encoder 138 is an angle encoder that outputs an opening angle θ1 of the operation part 105, i.e., the angle θ1 made by the first operation part 103 and the second operation part 104. The opening angle of the operation part 105 is linked to an opening angle θ2 of the pinching part 140 (a first pinching part 142 and a second pinching part 143). Thus, by detecting the opening angle θ1 of the operation part 105 with the encoder 138, it is possible to find the opening angle θ2 of the pinching part 140. Note that, in a case where an opening/closing motion of the operation part 105 is converted, inside the main body 110, into a linear motion of the shaft and then is transmitted as an opening/closing motion of the pinching part 140, a liner encoder may be employed as the encoder 138. In this case, the opening angle θ2 of the pinching part 140 can be calculated on the basis of an amount of movement of the shaft output by the linear encoder. Instead of the opening angle θ2 of the pinching part 140, a distance between the first pinching part 142 and the second pinching part 143 may be calculated.

On the basis of the opening angle of the pinching part 140 or the distance between the first pinching part 142 and the second pinching part 143, the correction part 137 corrects a detection efficiency (detection sensitivity) of concurrent counting of annihilation gamma rays carried out by the first scintillator 144 and the second scintillator 145. The positional relation between the two scintillators 144 and 145 varies depending on the opening angle of the pinching part 140. The correction part 137 corrects the detection efficiency of the concurrent counting in accordance with the positional relation between the two scintillators 144 and 145, so as to prevent a phenomenon that radioactivity to be detected varies when the opening angle of the pinching part 140 changes.

As shown in (a) of FIG. 12, when the opening angle of the operation part 105 is maximum, the opening angle of the pinching part 140 is maximum. As the opening angle of the operation part 105 decreases, the opening angle of the pinching part 140 decreases. For example, assume that detection of annihilation gamma rays is carried out with a lymph node S pinched by the pinching part 140. Then, if the lymph node S is large, the opening angle of the pinching part 140 is large, as shown in (b) of FIG. 12. Meanwhile, if the lymph node S is small, the opening angle of the pinching part 140 is small, as shown in (c) of FIG. 12. Thus, by tightly pinching the lymph node S by the pinching part 140, it is possible to detect annihilation gamma rays as well as to measure the size of the lymph node S on the basis of the opening angle of the pinching part 140 or the distance between the first pinching part 142 and the second pinching part 143.

For example, assuming that the lymph node S has a spherical shape, it is possible to find a diameter of the lymph node S on the basis of the opening angle of the pinching part 140 or the distance between the first pinching part 142 and the second pinching part 143, and to calculate a volume (ml). Meanwhile, a value (cps) of the concurrent counting carried out by the two scintillators 144 and 145 can be corrected by the correction part 137, and the value thus corrected can be converted into an amount (becquerel) of radioactivity of the lymph node S. On the basis of these results, it is possible to calculate a radioactivity density (becquerel/ml) of the lymph node S. The radioactivity density of the lymph node S is proportional to an accumulation density of radionuclides. Thus, it is possible to estimate an amount of cancer cells in the lymph node S.

As discussed above, use of the encoder 138 makes it possible to calculate the opening angle of the pinching part 140. Then, by correcting the detection efficiency of the two scintillators 144 and 145 provided in the pinching part 140 on the basis of the opening angle of the pinching part 140, it is possible to calculate a more accurate radioactivity amount of a target to be measured. Furthermore, on the basis of the opening angle of the pinching part 140, it is possible to find the size of the target to be measured. Moreover, on the basis of the radioactivity amount and the size of the target to be measured, it is possible to calculate the radioactivity density of the target to be measured.

Next, the following description will discuss an example of use of the radiation detector 3. On the basis of a change in the opening angle of the pinching part 140 or a change in the distance between the first pinching part 142 and the second pinching part 143, the control part 50 can carry out control for opening and/or ending operation of the above-described radiation detector. For example, radiation measurement may be started when the opening angle of the pinching part 140 (i.e., the opening angle of the operation part 105) that was closed in the beginning becomes maximum. That is, the control part 50 may be configured to start radiation measurement at a time when the opening angle of the pinching part 140 changes from a non-maximum state to a maximum state.

Further, the control part 50 may be configured to end radiation measurement when a given condition is satisfied. For example, the control part 50 may be configured to end the measurement at a time when a given period of time has elapsed since the start of the measurement. Alternatively, the measurement may be ended when, after the opening angle of the pinching part 140 changes in accordance with the size of the lymph node, the opening angle of the pinching part 140 changes again. This configuration may be employed, since it is considered that the above phenomenon means that the measurement work on the lymph node has been ended and the lymph node has been released. Alternatively, the measurement may be ended when the opening angle of the pinching part 140 becomes minimum (closed). This configuration may be employed, since it is considered that the above phenomenon means that the measurement work has been ended. Note that, even after the measurement is ended, it is possible to start the measurement again by making the opening angle of the pinching part 140 maximum again.

As discussed above, with the radiation detector 3 so configured to autonomously start and end radiation measurement on the basis of a given condition, the operator does not need to operate a button for starting/ending the measurement, which enables to carry out a surgery smoothly.

Next, the following description will discuss, with reference to FIG. 13, an example of control to be carried out by the radiation detector 3 to start and end radiation measurement. As shown in FIG. 13, first, the control part 50 uses the encoder 138 to measure an opening angle of the pinching part 140 (step S201). Next, the control part 50 determines whether or not the opening angle of the pinching part 140 is a maximum angle (step S202). If the opening angle of the pinching part 140 is the maximum angle (step S202: YES), the control part 50 starts radiation measurement (step S203). If the opening angle of the pinching part 140 is not the maximum angle (step S202: NO), the control flow returns to step S201. Next, in step S204, after the control part 50 starts the radiation measurement, the control part 50 constantly measures an opening angle of the pinching part 140. Then, the control part 50 corrects a detection efficiency of the two scintillators 144 and 145 on the basis of the opening angle of the pinching part 140 thus measured (step S205), and calculates a radioactivity value (step S207). In parallel with steps S205 and S207, the control part 50 calculates a diameter of the target (step S206). Then, the control part 50 determines whether or not an end condition of the radiation measurement is satisfied (step S209). If it is determined in step S209 that the end condition is not satisfied (step S209: NO), the control flow returns to step S204. If it is determined in step S209 that the end condition is satisfied (step S209: YES), the control part 50 records the measured maximum radioactivity value and the diameter of the target (step S210), and ends the radiation measurement. After that, the control flow may return to step S201.

The end condition used in step S209 can be set as appropriate. For example, the end condition may be, as described above, (i) that a given period of time has elapsed since start of measurement, (ii) that, after the opening angle of the pinching part 140 changes, the opening angle of the pinching part 140 changes again, or (iii) that the opening angle of the pinching part 140 becomes minimum. In Embodiments 2 and 3 discussed above, the F-18 labeling FDG is indicated as an example of the medicament containing the radionucides. However, the medicament is not limited to this. Further, in Embodiments 1 to 3, the lymph node is indicated as an example of a body tissue for which whether or not medicaments containing radionuclides are accumulated is determined. However, the tissue is not limited to this.

Embodiment 4

Shape of Scintillator

Next, the following description will discuss, with reference to the drawings, a radiation detector configured as a grasping forceps for a surgery in accordance with Embodiment 4 of the present invention. A configuration of the radiation detector in accordance with Embodiment 4 is substantially identical to a configuration of the radiation detector 3 in accordance with Embodiment 3. Differences therebetween are the parts discussed below. Note that elements having identical configurations to those of the foregoing embodiments are given identical reference signs, and their descriptions will be omitted.

The radiation detector in accordance with Embodiment 4 may be inserted into a body via, for example, a trocar. The trocar is a medical tool used for chest drainage, for example. Use of the trocar makes it possible to provide a therapeutic method having a lower degree of invasion. However, a diameter of the trocar is not so large, for example, approximately 5 mm to several tens of mm. Thus, from the viewpoint of the detection efficiency of radiation, it is preferable that each of the scintillators 144 and 145 in a single set have a shape that can be housed inside a commercially-available trocar and have as large cross-sectional area as possible in a direction orthogonal to an insertion direction. The trocar has a circular cross-section, and therefore it is preferable that each of the scintillators 144 and 145 in a single set also have a circular cross-section in order to have as large cross-sectional area as possible. Employing such a configuration increases the volumes of the scintillators that can detect radiation, thereby making it possible to increase the radiation detection efficiency.

FIG. 14 illustrates cross-sections of the first scintillator 144 and the second scintillator 145 respectively housed in a first pinching part 142 and a second pinching part 143 of the radiation detector in accordance with Embodiment 4, the cross-sections being taken along a direction orthogonal to longitudinal directions of the first scintillator 144 and the second pinching part 145. As shown in FIG. 14, each of the first scintillator 144 and the second scintillator 145 has a semicircular cross-sectional shape, and the two scintillators 144 and 145 are arranged to face each other so as to form a circular shape.

Also in a pinching part 140 of the radiation detector in accordance with Embodiment 4, each of a first pinching part 142 and a second pinching part 143 has a semicircular shape, and the first pinching part 142 and the second pinching part 143 form a circular shape when closed.

In this case, a size of each of the scintillators 144 and 145 and a size (diameter) of the entire radiation detector in accordance with Embodiment 4 are set so as to be insertable into a body via an existing trocar. That is, these sizes are set so as to allow the radiation detector in which the scintillators 144 and 145 are housed to pass through the trocar. With the above configuration, it is possible to provide, with use of an existing trocar, a radiation detector capable of carrying out a diagnosis and a treatment with a low degree of invasion.

Embodiment 5

Preset Counting Method

Next, the following description will discuss, with reference to the drawings, a method in accordance with Embodiment 5 to be carried out by a radiation detector to count radiation. A configuration of a radiation detector in accordance with Embodiment 5, which is configured as a grasping forceps for a surgery, is substantially identical to the configuration of the radiation detector 3 in accordance with Embodiment 3. Differences therebetween are the parts discussed below. Note that elements having identical configurations to those of the foregoing Embodiments are given identical reference signs, and their descriptions will be omitted.

In some cases, many targets to be measured (measurement targets) exist when a user (surgical operator) carries out radioactivity measurement on an affected site with use of a radiation detector during a surgery. For example, in a case where measurement is carried out on cancerous lymph nodes, it is necessary to carry out measurement by pinching, with the pinching part 140, a large number of lymph nodes one by one. In such a case, the measurement may be carried out by a preset counting method. By carrying out the measurement by the preset counting method, it is possible to shorten a measurement period taken in a case where an affected site has high radioactivity. The preset counting method is effective when measurement is carried out on a large number of lymph nodes. The preset counting method can suppress increase in surgery time that may otherwise be caused by radiation measurement carried out in the surgery.

The preset counting is carried out in the following manner. FIG. 15 is a flowchart of a measurement method to be carried out by a control part 50 of the radiation detector in accordance with Embodiment 5. As shown in FIG. 15, after measurement is started, the control part 50 integrates count values in step S300. The integrated count value indicates the number of times of detection of radiation. Then, in step S301, the control part 50 determines whether or not the integrated count value is equal to or more than a set value that is set in advance. If it is determined in step S301 that the integrated value is equal to or more than the set value (step S301: Y), the process transitions to step S303. In step S303, the control part 50 notifies (reports) the user that the integrated count value is equal to or more than a reference value, and ends the measurement. The expression that "the control part 50 notifies the user that the count value is equal to or more than the reference value" means that the control part 50 causes the light emitting part 130 to emit light by a given method.

Meanwhile, if it is determined in step S301 that the integrated value is not equal to or more than the set value (step S301: N), the process transitions to step S302. In step S302, the control part 50 determines whether or not a given measurement period has elapsed. If it is determined in step S302 that the given measurement period has not elapsed (step S302: N), the process returns to step S300. Meanwhile, if it is determined in step S302 that the given measurement period has elapsed (step S302: Y), the process transitions to step S304. In step S304, the control part 50 notifies the user that the integrated value is less than the reference value, and ends the measurement.

The reference value is set by the user in advance on the basis of an indicator related to a degree of malignancy of the affected site. That is, the control part 50 notifies a result of comparison between the measured radiation value and the indicator related to the degree of malignancy of the affected site.

Specifically, for example, the reference value is a count value indicating a probability of metastasis of a cancer from an affected site. The inventors of the present invention found that a radioactivity amount of a lymph node is correlated with a probability of metastasis, i.e., that, in a case where a radioactivity amount of a lymph node is equal to or more than a first value, the probability of metastasis is high. Specifically, the inventors found that, in a case where a radioactivity amount of a single lymph node is equal to or more than 10000 (Bq), the probability of metastasis is high. The user can convert such a radioactivity amount into an integrated count value obtained when measurement is carried out for a given period of time with use of given scintillators 144 and 145 of a radiation detector, and can set the integrated count value as the reference value.

Alternatively, the reference value may be a count value considered to indicate a low probability of metastasis of a cancer. The inventors found that, in a case where a radioactivity amount of a lymph node is equal to or less than a second value, the probability of metastasis is low. Specifically, the inventors found that, in a case where a radioactivity amount of a single lymph node is equal to or less than 600 (Bq), the probability of metastasis is low. The user may convert such a radioactivity amount into an integrated count value obtained for a given period of time, and may set the integrated count value as the reference value.

For example, in a case where 185 (MBq) of FDG is administered to a cancer patient and radioactivity measurement is carried out 6 hours after the administration, an amount of radioactivity accumulated therein is expected as below, although this may vary depending on the sizes and shapes of the scintillators 144 and 145 and the structure of the pinching part 140. That is, in a case of a radioactivity amount (a radioactivity amount of 600 (Bq) per lymph node) of a lymph node considered to have a low probability of metastasis, it is expected that 100 counts will be measured for 30 seconds. Meanwhile, in a case of a radioactivity amount (a radioactivity amount of 10000 (Bq) per lymph node) of a lymph node considered to have a high probability of metastasis, it is expected that 100 counts will be measured for 1.8 seconds.

For example, assume that the reference value of the radioactivity amount is set at 600 (Bq), the set value of the measured value is set at 100 counts, and the given measurement period is set at 30 seconds. Then, if a measured value does not reach the set value even after the measurement period (30 seconds) has elapsed, it is determined that a radioactivity amount of that lymph node is equal to or less than 600 (Bq) and the probability of metastasis is low. Meanwhile, if a measured value becomes equal to or less than the set value in a period equal to or less than 1.8 seconds, it is possible to determine that the probability of metastasis in that lymph node is high.

By measuring the radioactivity in this manner, notification of the lymph node having a large radioactivity amount is made in short time and the measurement is ended. Thus, even in a case where measurement is carried out on a large number of lymph nodes, the measurement time can be shortened. Further, with a configuration in which notification is made immediately after the end of measurement or a period of time taken from the end of measurement to notification is always constant, a user can acknowledge an approximate radioactivity amount on the basis of the period of time taken from the start of the measurement to the end of the measurement. Note that the reference values of the measurement period and the integrated count value can be set as appropriate on the basis of (i) an amount of radionuclides expected to be accumulated in an affected site and (ii) a detection efficiency of the scintillators 144 and 145 of the radiation detector.

It is preferable that the method in which the control part 50 gives notification to the user be made different between (i) a case where the notification notifies that a value of interest is equal to or more than the reference value and (ii) a case where the notification notifies that a value of interest is less than the reference value. For example, in a case where a value of interest is less than the reference value, the control part 50 can maintain an illuminated state of light emission. Meanwhile, in a case where a value of interest is equal to or more than the reference value, the control part 50 can change the state of light emission from an illuminated state to a flashing state. In this manner, it is possible to notify the user that the value of interest becomes equal to or more than the reference value. A flashing period may be set constant. If the illuminated state is maintained even after the measurement is ended, this means that the value of interest is less than the reference value. If the light emission changes into a flashing state in short time, this means that a radioactivity amount is large. Alternatively, the notification method may be a method involving use of a sound or a method involving use of a combination of a sound and light.

Variations

Alternatively, the following measurement method may be employed. FIG. 16 is a flowchart illustrating a measurement method in accordance with a variation of Embodiment 5. The flowchart shown in FIG. 16 indicates a flow of calculation of an amount of radioactivity accumulated in a lymph node and notification of a result of the calculation to a user. As shown in FIG. 16, after measurement is started, the control part 50 first integrates counts in step S310. Then, in step S311, the control part 50 determines whether or not the integrated count value is equal to or more than a set value that is set in advance.

If it is determined in step S311 that the integrated value is equal to or more than the set value (step S311: Y), the process transitions to step S314. In step S314, the control part 50 stops a timer. Then, in step S315, the control part 50 calculates a radioactivity amount of a lymph node on the basis of the count value. The radioactivity amount of the lymph node is found by conversion of the count value in accordance with the shapes of the scintillators 144 and 145, an opening angle of the radiation detector, the size of the affected site, and/or the like. Then, in step S316, the control part 50 notifies the user of the radioactivity amount, and ends the measurement.

Meanwhile, if it is determined in step S311 that the integrated value is not equal to or more than the set value (step S311: N), the process transitions to step S312. In step S312, the control part 50 determines whether or not a given measurement period has elapsed. If it is determined in step S312 that the given measurement period has not elapsed (step S312: N), the process returns to step S310. Meanwhile, if it is determined in step S312 that the given measurement period has elapsed (step S312: Y), the process transitions to step S313. In step S313, the control part 50 notifies the user that the integrated value is less than the reference value, and ends the measurement.

By measuring the radioactivity by such a method, notification of the lymph node having a large radioactivity amount is made in short time and the measurement is ended. Thus, even in a case where measurement on a large number of lymph nodes is carried out, the measurement time can be shortened.

The notification to the user may be carried out by a similar method to that discussed in the foregoing example. A frequency of flashing may be changed. For example, in a case where the radioactivity amount of the lymph node is large, the frequency of the flashing may be increased. Meanwhile, in a case where the radioactivity amount of the lymph node is small, the frequency of the flashing may be decreased.

Note that the method for giving an instruction to start measurement of a radioactivity amount may be selected from many methods. For example, the measurement may be started in response to a motion of the radiation detector. Specifically, for example, a sensor capable of detecting a degree of opening of the pinching part 140 of the radiation detector may be attached. With this, the measurement may be started when the pinching part 140 changes from a completely closed state to an opened state. For another example, a tactile sensor may be provided to, e.g., the distal end of the pinching part 140. With this, the measurement may be started when the tactile sensor senses contact with a lymph node (measurement target). For still another example, a speech recognition system that can detect a user's voice may be provided. With this, the measurement may be started when a certain voice (e.g., a voice uttering "start") of a user is recognized.

Alternatively, for example, the pinching part 140 may indicate a degree of opening of the pinching part 140. With this, the user can determine a timing to start the measurement. In a case where the pinching part 140 indicates the degree of opening, it is preferable that a display part that indicate the degree of opening be positioned at a location that can be seen by a user during normal operation. A purpose of this is to eliminate the need for changing the orientation of the radiation detector when the user checks the degree of opening.

As discussed above, with a configuration in which the measurement is started autonomously under a certain condition, it is possible to reduce the burden on a user and shorten a period of time until the start of the measurement, as compared to a configuration in which the measurement is started by the user's operating a switch.

Aspects of the present invention can also be expressed as follows:

A radiation detector in accordance with aspect 1 of the present invention includes: at least one probe which has a radiation detection element housed therein and which is insertable into a body; a reporting part provided to the at least one probe; and a control part configured to cause the reporting part to operate in accordance with a result of detection of radiation, the detection being made by the radiation detection element.

With the above configuration, it is possible to allow an operator to more correctly identify a position of a body tissue into which radionuclides have been taken. To be more specific, while operating the probe, the operator (surgical operator) can identify, on the basis of report information from the reporting part, a position of a radiation source (affected site) in which radionuclides are accumulated. Further, since the reporting part is provided in the probe, which has the radiation detection element housed therein, the operator can identify the position of the affected site even without changing the orientation of his/her face or the direction of his/her sightline.

Note that the present invention can also provide, for example, a method for detecting radiation, including the steps of: detecting radiation by a radiation detection element provided to a probe inserted into a body; and causing a reporting part, which is further provided to the probe, to operate on a basis of a result of the detection of the radiation.

A radiation detector in accordance with aspect 2 of the present invention may further include: a setting part configured to set, for the control part, a threshold that is used to determine whether to cause the reporting part to operate and that corresponds to the result of the detection.

With the above configuration, radioactivity to be detected varies depending on, e.g., a type of a radionuclide to be used, an amount of a radionuclide to be administered, or an amount of accumulated radionuclides. By changing, depending on the situation, a threshold used to cause the reporting part to operate, it is possible to deal with various clinical situations.

A radiation detector in accordance with aspect 3 of the present invention may be configured such that: the reporting part is at least one light emitting part provided to an outer surface of the at least one probe.

With the above configuration, in which the reporting part is the light emitting part, it is possible to visually identify the position of the affected site.

A radiation detector in accordance with aspect 4 of the present invention may be configured such that: the control part controls the at least one light emitting part so that, on a basis of a count or a counting rate of the radiation obtained as the result of the detection, the at least one light emitting part changes at least one selected from the group consisting of an intensity of light emission, a pattern of light emission, a color of light emission, and a period of light emission.

With the above configuration, the operator can visually recognize the radioactivity in accordance with the mode of light emission of the light emitting part. Therefore, the operator can easily identify a position and a range where radionuclides are accumulated, i.e., a position and a range of the affected site.

A radiation detector in accordance with aspect 5 of the present invention may be configured such that: the at least one light emitting part and a light emitting element that causes the at least one light emitting part to emit light are disposed so as to be spaced from each other, and the light emitting element and the at least one light emitting part are optically coupled to each other via an optical fiber.

With the above configuration, the light emitting element is disposed at a location spaced from the probe. This can reduce the size of the probe.

A radiation detector in accordance with aspect 6 of the present invention may be configured such that: the at least one light emitting part is disposed continuously so as to surround an outer peripheral surface of the at least one probe, the at least one light emitting part at least partially protrudes from the outer surface of the at least one probe, or the at least one light emitting part includes a plurality of light emitting parts disposed at respective of a plurality of positions on the outer surface of the at least one probe.

With the above configuration, light from the light emitting part is emitted at a wide solid angle or rays of light are emitted from the light emitting parts at the plurality of positions. Therefore, even when the orientation or position of the probe changes, the operator can easily recognize presence or absence of light emission.

A radiation detector in accordance with aspect 7 of the present invention may further include: a collimator configured to regulate an incident direction of radiation that enters the radiation detection element.

With the above configuration, it is possible to suppress, by the collimator, a phenomenon that radiation from the surrounding environment enters the radiation detection element. This makes it possible to efficiently detect radiation from the affected site, thereby efficiently detecting the position of the affected site.

A radiation detector in accordance with aspect 8 of the present invention may be configured such that: the radiation detection element is a detection element for a Compton camera.

With the above configuration, it is possible to efficiently detect radiation from the affected site by the Compton camera system, without use of a collimator or a shield. This makes it possible to efficiently detect the position of the affected site.

A radiation detector in accordance with aspect 9 of the present invention may be configured such that: the radiation detection element is a radiation detection element employing a concurrent counting system.

With the above configuration, in a case of using a radionuclide that discharges a gamma ray due to annihilation of a set of a positron and an electron, use of the radiation detection element of the concurrent counting system enables efficient detection of the affected site.

A radiation detector in accordance with aspect 10 of the present invention may be configured such that: the at least one probe includes two probes, and each of the two probes has a radiation detection element housed therein.

With the above configuration, in which the two probes each including the radiation detection element are provided, it is possible to make use of the features of the concurrent counting system for radiation.

A radiation detector in accordance with aspect 11 of the present invention may be configured such that: the radiation detector is configured as a grasping forceps for a surgery, and the grasping forceps has two distal ends respectively functioning as the probes each provided with the radiation detection element.

With the above configuration, in which the radiation detector is configured as a grasping forceps for a surgery, it is possible to more easily identify the position of the affected site during a surgery.

A radiation detector in accordance with aspect 12 of the present invention is a radiation detector configured as a grasping forceps for a surgery, the grasping forceps being insertable into a body, the grasping forceps having two distal ends respectively configured as two probes each having a radiation detection element housed therein, the radiation detector including: a reporting part provided to the grasping forceps; and a control part configured to cause the reporting part to operate in accordance with a result of detection of annihilation gamma rays, the detection being made by concurrent counting carried out by the radiation detection elements respectively housed in the two probes.

The above configuration eliminates the need for pinching a body tissue by a grasping forceps, measuring radiation from radionuclides taken into the body tissue, and the operator seeing a given display screen or the like capable of indicating, e.g., a nuclide distribution image or a radioactivity value. This makes it possible to allow the operator to more correctly recognize whether or not the radionuclides are accumulated in the body tissue.

Note that the present invention can also provide, for example, a method for detecting radiation with use of a radiation detector configured as a grasping forceps for a surgery, the grasping forceps being insertable into a body, the method including the steps of: detecting annihilation gamma rays in accordance with a concurrent counting system, with use of the radiation detection elements respectively provided to the two probes constituted by respective distal ends of the grasping forceps inserted into the body; and causing a reporting part provided to the grasping forceps to operate on a basis of a result of the detection of the annihilation gamma rays.

A radiation detector in accordance with aspect 13 of the present invention may be configured such that: the control part corrects a detection sensitivity of the concurrent counting on a basis of an opening angle made by the two probes or a distance between the two probes.

With the above configuration, it is possible to accurately measure radioactivity of the affected site.

A radiation detector in accordance with aspect 14 of the present invention may be configured such that: the control part measures a size of a measurement target on a basis of an opening angle made by the two probes or a distance between the two probes.

With the above configuration, it is possible to detect not only the position of the affected site but also the size of the affected site.

A radiation detector in accordance with aspect 15 of the present invention may be configured such that: the control part calculates a volume of a measurement target on a basis of an opening angle made by the two probes or a distance between the two probes, and calculates radioactivity per volume.

With the above configuration, it is possible to detect not only the position of the affected site but also an accumulation density of the radionuclides, i.e., a degree of dispersion of the affected site.

A radiation detector in accordance with aspect 16 of the present invention may be configured such that: the control part carries out control for starting and/or ending operation of the radiation detector on a basis of a change in the opening angle made by the two probes or a change in the distance between the two probes.

The above configuration eliminates the need for the operator to carry out operation for starting and stopping the radiation detector, thereby enhancing the work efficiency in a diagnosis or a therapy.

A radiation detector in accordance with aspect 17 of the present invention may be configured such that: the reporting part is a light emitting part, and is disposed in (i) at least one of the two probes or (ii) a main body of the grasping forceps.

The above configuration eliminates the need to see a separated display screen while carefully looking at the probes of the grasping forceps. Thus, it is possible to allow the operator to more correctly recognize whether or not the radionuclides are accumulated in the body tissue.

A radiation detector in accordance with aspect 18 of the present invention may be configured such that: the radiation detection elements respectively housed in the two probes each have a semicircular cross-sectional shape.

With the above configuration, it is possible to increase the volume of the radiation detection elements, thereby enhancing the detection efficiency.

A radiation detector in accordance with aspect 19 of the present invention may be configured such that: the reporting part gives a report reporting a result of comparison between the result of the detection of the annihilation gamma rays and an indicator regarding a degree of malignance of an affected site.

With the above configuration, a user can easily recognize the degree of malignance of the affected site in accordance with the reporting mode of the reporting part.

A radiation detector in accordance with aspect 20 of the present invention may be configured such that: the control part is disposed in another housing that is not a main body of the radiation detector.

With the above configuration, even in a case where the control part has a large workload and requires a larger size, it is possible to eliminate the possibility of impairment in operability of the radiation detector that is to be operated with grasped with a hand.

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST 1, 1A, 2, 3: radiation detector
10: probe
20: radiation detection element
22, 134: optical fiber
30, 130: light emitting part (reporting part)
32, 132: light emitting element
40: light receiving part (amplifying part)
50: control part
52: processor
54: memory
56: bus
62: input-output interface (I/O)
64: setting part
66: counting part
70: input part
80, 105: operation part
82: cable
103: first operation part
104: second operation part
110: main body
120: first light receiving element (amplifying part)
121: second light receiving element (amplifying part)
122: first optical fiber
123: second optical fiber
136: concurrent count circuit
137: correction part
138: encoder
140: pinching part (probe)
142: first pinching part
143: second pinching part
144: first scintillator (radiation detection element)
145: second scintillator (radiation detection element)
160: opening/closing shaft
200: optical camera

The invention claimed is:

1. A radiation detector comprising:
two probes, wherein each of the two probes has a radiation detection element housed therein and is insertable into a body, wherein the radiation detection element is a radiation detection element employing a concurrent counting system;
a reporting part provided to the two probes; and
a control part configured to cause the reporting part to operate in accordance with a result of detection of radiation, the detection being made by the radiation detection element respectively housed in the two probes, wherein the control part corrects a detection sensitivity of the concurrent counting on a basis of an opening angle made by the two probes or a distance between the two probes.

2. The radiation detector as set forth in claim 1, further comprising:
a setting part configured to set, for the control part, a threshold that is used to determine whether to cause the reporting part to operate and that corresponds to the result of the detection.

3. The radiation detector as set forth in claim 1, wherein:
the reporting part is at least one light emitting part provided to an outer surface of at least one probe of the two probes.

4. The radiation detector as set forth in claim 3, wherein:
the control part controls the at least one light emitting part so that, on a basis of a count or a counting rate of the radiation obtained as the result of the detection, the at least one light emitting part changes at least one selected from the group consisting of an intensity of light emission, a pattern of light emission, a color of light emission, and a period of light emission.

5. The radiation detector as set forth in claim 3, wherein:
the at least one light emitting part and a light emitting element that causes the at least one light emitting part to emit light are disposed so as to be spaced from each other, and the light emitting element and the at least one light emitting part are optically coupled to each other via an optical fiber.

6. The radiation detector as set forth in claim 3, wherein:
the at least one light emitting part is disposed continuously so as to surround an outer peripheral surface of at least one probe of the two probes, the at least one light emitting part at least partially protrudes from the outer surface of the at least one probe of the two probes, or the at least one light emitting part comprises a plurality of light emitting parts disposed at respective of a plurality of positions on the outer surface of the at least one probe of the two probes.

7. The radiation detector as set forth in claim 1, further comprising:
a collimator configured to regulate an incident direction of radiation that enters the radiation detection element.

8. The radiation detector as set forth in claim 1, wherein:

the radiation detection element is a detection element for a Compton camera.

9. The radiation detector as set forth in claim 1, wherein: the radiation detector is configured as a grasping forceps for a surgery, and the grasping forceps has two distal ends respectively functioning as the probes each provided with the radiation detection element.

10. A radiation detector configured as a grasping forceps for a surgery, the grasping forceps being insertable into a body, the grasping forceps having two distal ends respectively configured as two probes each having a radiation detection element housed therein, said radiation detector comprising:

a reporting part provided to the grasping forceps; and a control part configured to cause the reporting part to operate in accordance with a result of detection of annihilation gamma rays, the detection being made by concurrent counting carried out by the radiation detection elements respectively housed in the two probes, wherein the control part is further configured to correct a detection sensitivity of the concurrent counting on a basis of an opening angle made by the two probes or a distance between the two probes.

11. The radiation detector as set forth in claim 10, wherein:

the control part measures a size of a measurement target on a basis of an opening angle made by the two probes or a distance between the two probes.

12. The radiation detector as set forth in claim 10, wherein:

the control part calculates a volume of a measurement target on a basis of an opening angle made by the two probes or a distance between the two probes, and calculates radioactivity per volume.

13. The radiation detector as set forth in claim 10, wherein:

the control part carries out control for starting and/or ending operation of the radiation detector on a basis of a change in the opening angle made by the two probes or a change in the distance between the two probes.

14. The radiation detector as set forth in claim 10, wherein:

the reporting part is a light emitting part, and is disposed in (i) at least one of the two probes or (ii) a main body of the grasping forceps.

15. The radiation detector as set forth in claim 10, wherein:

the radiation detection elements respectively housed in the two probes each have a semicircular cross-sectional shape.

16. The radiation detector as set forth in claim 10, wherein:

the reporting part gives a report reporting a result of comparison between the result of the detection of the annihilation gamma rays and an indicator regarding a degree of malignance of an affected site.

17. The radiation detector as set forth in claim 1, wherein: the control part is disposed in another housing that is not a main body of the radiation detector.

\* \* \* \* \*